(12) United States Patent
Morris et al.

(10) Patent No.: US 6,328,567 B1
(45) Date of Patent: Dec. 11, 2001

(54) METHOD, APPARATUS AND SYSTEM FOR AUTOMATED TOOTH SHADE ANALYSIS AND MATCHING

(75) Inventors: Alan C. Morris, Salt Lake City, UT (US); Craig A. Mabrito, Belair, TX (US)

(73) Assignee: DenTech, LLC, Salt Lake City, UT (US)

( * ) Notice: Subject to any disclaimer, the term of this patent is extended or adjusted under 35 U.S.C. 154(b) by 0 days.

(21) Appl. No.: 09/477,777

(22) Filed: Jan. 4, 2000

Related U.S. Application Data

(63) Continuation-in-part of application No. 09/234,585, filed on Jan. 21, 1999, now Pat. No. 6,190,170.

(51) Int. Cl.[7] .............................. A61C 5/00; A61C 19/10; A61C 13/08
(52) U.S. Cl. ........................ 433/215; 433/26; 433/203.1
(58) Field of Search .................................. 433/215, 223, 433/226, 229, 26

(56) References Cited

U.S. PATENT DOCUMENTS

| | | |
|---|---|---|
| 3,986,777 | 10/1976 | Roll . |
| 4,110,826 | 8/1978 | Mollgaard et al. . |
| 4,654,794 | 3/1987 | O'Brien . |
| 4,813,000 | 3/1989 | Wyman et al. . |
| 5,055,040 | 10/1991 | Clar . |
| 5,383,020 | 1/1995 | Vieillefosse . |
| 5,529,492 | 6/1996 | Yarovesky et al. . |
| 5,690,486 | 11/1997 | Zigelbaum . |
| 5,745,229 | 4/1998 | Jung et al. . |
| 5,759,030 | 6/1998 | Jung et al. . |
| 5,766,006 | 6/1998 | Murljacic . |
| 5,961,324 | 10/1999 | Lehmann . |

FOREIGN PATENT DOCUMENTS 4-338465  11/1992  (JP) .

OTHER PUBLICATIONS

International Search Report, dated Jul. 16, 1999.

*Primary Examiner*—Nicholas D. Lucchesi
(74) *Attorney, Agent, or Firm*—TraskBritt

(57) ABSTRACT

Methods, apparatuses and systems for tooth shade analysis and matching are disclosed. A method embodiment according to the invention includes acquiring at least one image, the image including one or more teeth of a patient and normalization references, normalizing the at least one image in accordance with the normalization references, determining the color of the teeth as composed of colors from one or more selected shade standards, communicating the standardized color information to a dental laboratory, manufacturing a dental prosthesis based on the standardized color information and installing the dental prosthetic. Normalization is performed to correct patient images for variations in lighting conditions and image source. Normalization references include a black reference, a white reference and at least one color reference. The normalized image is standardized by matching the pixels of the normalized image to selected shade standards. Selected shade standards may include incisal tooth shade standards. The standardized color image and/or analysis may be communicated to a dental laboratory according to aspects of the invention. The dental prosthesis can then be manufactured by a lab technician by referring to the standardized image. Color models according to the invention may include RGB, HSI and other models for representing color images. The methods, apparatuses and systems for tooth shade analysis and matching are also applicable to direct restorations of natural teeth, such as repair of chipped or broken teeth.

35 Claims, 27 Drawing Sheets

Fig. 4

METHOD, APPARATUS AND SYSTEM FOR AUTOMATED TOOTH SHADE ANALYSIS AND MATCHING

CROSS-REFERENCE TO RELATED APPLICATION

This is a continuation-in-part application of U.S. patent application, Ser. No. 09/234,585, titled AUTOMATED TOOTH SHADE MATCHING SYSTEM, filed Jan. 21, 1999, now U.S. Pat. No. 6,190,170 issued Feb. 20, 2001.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates generally to systems for color matching and, more particularly, to systems for analyzing and matching tooth shades. Such systems are of particular use in manufacturing dental prosthetics (e.g., crowns, bridges, veneers, and prosthetic teeth) to repair, replace or alter natural teeth, in various dental tooth whitening procedures and to enable communication between patient, dentist and lab technician concerning such procedures.

2. Description of the Related Art

Dentists often repair or replace a diseased, damaged, or unsightly natural tooth of a patient with a crown, bridge, veneer, or prosthetic tooth. One obvious goal in performing such a repair or replacement is to provide the patient with a natural-looking smile despite the presence of the prosthesis. Attempts to reach this goal generally involve matching the color of the prosthesis to the color of the natural tooth being repaired or replaced, and to the colors of the natural teeth that are adjacent where the prosthesis will be placed.

Similarly, dentists often perform various tooth whitening procedures on a patient's natural teeth to reverse the effects of aging, coffee drinking, smoking, and similar activities on the patient's dental appearance. The goal in such procedures is also to provide the patient with a natural-looking smile, and attempts to reach this goal also generally involve color matching.

To this end, manufacturers of the various colored porcelains, resins, compomers ceramers or other direct restorative materials conventionally used in making dental prosthetics, or in repairing discolored, chipped, broken or malformed teeth, typically provide color matching shade guides to dentists which illustrate the various colored porcelains available. As shown in FIG. 1, one such shade guide 10 includes a variety of shade tabs 12, each made of a different colored porcelain available from a manufacturer. A dentist determines the color of a patient's natural teeth by detaching individual shade tabs 12 from the shade guide 10 and holding the shade tabs 12 next to the patient's natural teeth for comparison. Once a color match is found, the dentist orders a dental prosthesis from a dental laboratory in the matching colored porcelain or other material, or, if the patient's teeth are being whitened, the dentist uses the color match as a base against which to compare the eventual results of the whitening process.

This somewhat rudimentary method often provides less than desirable results because of the inaccuracy inherent in the dentist "eyeballing" the color match. Poor lighting, poor vision, eye fatigue, conflicting ambient colors or even lack of patient cooperation in the process, among other things, can cause the dentist to miss the best match. More importantly, the best match is often a combination of two or more colored porcelains, sometimes from different manufacturers, which is difficult to discern by the human eye.

Accordingly, a variety of mechanical and electronic devices have been devised to aid in matching tooth shades. Some of these devices are described in U.S. Pat. No. 5,759,030 to Jung et al., U.S. Pat. No. 5,690,486 to Zigelbaum, U.S. Pat. No. 5,529,492 to Yarovesky et al., U.S. Pat. No. 5,383,020 to Vieillefosse, U.S. Pat. No. 5,055,040 to Clar, U.S. Pat. No. 4,654,794 to O'Brien, and U.S. Pat. No. 4,110,826 to Mollgaard. Unfortunately, none of these devices have been very successful in advancing the tooth shade matching process much beyond the "eyeballing" procedure described above.

Another approach to tooth shade matching is disclosed in JP 4-338465 to Eto, entitled, "Device for Adjusting the Shape and Tone of Prosthetic Teeth". This Japanese patent application discloses a device for adjusting the shape and color tone of prosthetic teeth including a still video camera or a charge coupled device (CCD) camera, an image processor, a video monitor, a printer, and a color tone table. As disclosed in JP 4-338465, a still image is taken of the patient's teeth. The image includes the missing or broken tooth and its symmetrical counterpart. The shape of the symmetrical counterpart is overlaid on the space or location of the missing or broken tooth. The color of the replacement tooth is obtained by color analysis of the remaining teeth on the missing tooth side of the patient's mouth and color tone signals from a digital table stored in advance. The results of the color analysis is a "mix composition" of the individual color tones of color tone adjusting agents for the material that the replacement for the missing tooth is to be constructed. The resulting prosthetic tooth according to JP 4-338465 is a homogenous mix of the individual color tones which may or may not have the appearance of a real tooth, which is usually not homogeneous. JP 4-338465 does not appear to disclose normalizing the digital images or the inclusion of a dental shade standard in the still image to assist in normalizing a digital image. Furthermore, JP 4-338465 does not appear to disclose color analysis of a digital image to obtain a picture of the prosthetic tooth with a map of the tooth shades that are required to match the surrounding teeth.

Yet another approach is disclosed in U.S. Pat. No. 5,766,006 to Murljacic. U.S. Pat. No. 5,766,006 discloses a tooth shade analyzer system and methods including a color CCD camera for capturing an image of a patient's tooth, a shade analyzer subsystem having color processing means for determining the color of the patient's tooth from the color information of the image obtained by the CCD camera, storage means for storing color shade standards, color correlation means for comparing the color of the patient's tooth with the stored shade standards to identify the color of the patient's tooth and means for communicating the color of the patient's tooth to a user of the system. U.S. Pat. No. 5,766,006 requires the same camera be used to capture the image of the patient's tooth and the dental shade standards to avoid having to normalize the color image. U.S. Pat. No. 5,766,006 is thus not capable of using images generated from any source and cannot normalize such arbitrary images using normalization standards. Furthermore, U.S. Pat. No. 5,766,006 does not appear to disclose color analysis of a digital image.

A variation on U.S. Pat. No. 5,766,006 is disclosed in U.S. Pat. No. 5,961,324 to Lehmann which is a continuation-in-part of the application from which U.S. Pat. No. 5,766,006 issued. U.S. Pat. No. 5,961,324 discloses a tooth shade analyzer system and methods including an intraoral camera and a tooth shade analyzer subsystem. The tooth shade analyzer subsystem includes color processing means for determining RGB chromacities of the color image of the patient's tooth and RGB chromacities of the stored tooth shades and means for comparing both. However, U.S. Pat. No. 5,961,324 does not disclose the use of other color models for digital color image analysis, such as hue, saturation, intensity (HSI). Furthermore, U.S. Pat. No. 5,961,324 requires the same camera be used to capture the image of the patient's tooth and the dental shade standards to avoid having to normalize the color image. Thus, the tooth shade analyzer disclosed in U.S. Pat. No. 5,961,324 is not capable of utilizing images generated from any source and cannot normalize such arbitrary images using normalization standards. In addition, U.S. Pat. No. 5,961,324 does not appear to disclose color analyzing the digital image to obtain a picture of the prosthetic tooth with a map of the tooth shades that are required to match the surrounding teeth.

Because of the limitations in the prior art as noted above, there exists a need in the art for a method, apparatus and system for an improved tooth shade matching system that does not require a CCD or other intraoral camera and thus can utilize an image from any source. Furthermore, a need exists in the art for a tooth shade analysis system that does not rely on RGB color models.

SUMMARY OF THE INVENTION

In accordance with the present invention, a computer-aided system, apparatus and methods for capturing an image of a patient's teeth and analyzing such image with respect to the inherent tooth coloration and shading characteristics of the patient's teeth for the purposes of reproducing such inherent coloration and shading in restorative procedures and prosthetics are disclosed.

In one embodiment of the invention, for example, a dental prosthesis for a patient is made by acquiring at least one image of the patient's teeth which contains normalization references. The image is then normalized in accordance with the normalization references. Next, the normalized image is standardized by matching the normalized image to selected shade standards, and the dental prosthesis is then made in accordance with the standardized image. The prosthesis may then be compared with the normalized image to assure a satisfactory product. The analysis and matching system of the present invention may be used not only in producing replacement prosthetics, such as dentures, bridges or caps, but is used in the restoration of broken, chipped or otherwise damaged or malformed teeth.

In another embodiment of this invention, a patient's teeth are whitened by acquiring at least one pre-whitening image of the patient's teeth, the image containing normalization references. The pre-whitening image is normalized in accordance with the normalization references contained therein, and the normalized pre-whitening image is then standardized by matching the normalized image to selected shade standards. The patient's teeth are then whitened. After whitening the patient's teeth, at least one post-whitening image of the patient's teeth containing normalization references is acquired, the post-whitening image is normalized in accordance with the normalization references contained therein, and the normalized post-whitening image is standardized by matching the normalized image to selected shade standards. Then, the standardized pre-whitening image and the standardized post-whitening image are compared to assess the degree of color matching.

In still another embodiment, image analysis is performed on a patient's teeth by acquiring at least one image of the patient's teeth containing normalization references. The image is then normalized in accordance with the normalization references contained therein, and the normalized image is standardized by matching the normalized image to selected shade standards. Communication between doctor, patient and lab technician is facilitated through the invention to provide each with the ability to select desired shades and/or colors of the eventual prosthesis, such as in cases of dental restoration where a full or partial set of dentures is being produced.

In a further embodiment of this invention, a computer-readable storage medium stores a program for causing a computer to operate in accordance with the method for performing image analysis on a patient's teeth described immediately above.

In yet another embodiment, an apparatus for performing image analysis on a patient's teeth includes an input device for acquiring at least one image of the patient's teeth, the image containing normalization standards. Another device coupled to the input device normalizes the image in accordance with the normalization references contained therein and matches the normalized image to selected shade standards to standardize the normalized image.

In an additional embodiment of this invention, an electronic system incorporates the apparatus described immediately above.

BRIEF DESCRIPTION OF DRAWINGS

In the drawings, which illustrate what is currently regarded as the best mode for carrying out the invention, and in which like reference numerals refer to like features in different views or embodiments:

FIG. 4 is a screen capture illustrating patient information entry 30 in accordance with FIG. 3.

BEST MODES FOR CARRYING OUT THE INVENTION

The following detailed description discloses a computer-aided system, apparatus and methods for capturing an image of a patient's teeth and analyzing such image with respect to the inherent tooth coloration and shading characteristics of the patient's teeth for the purposes of reproducing such inherent coloration and shading in restorative procedures and prosthetics.

Figure 2:
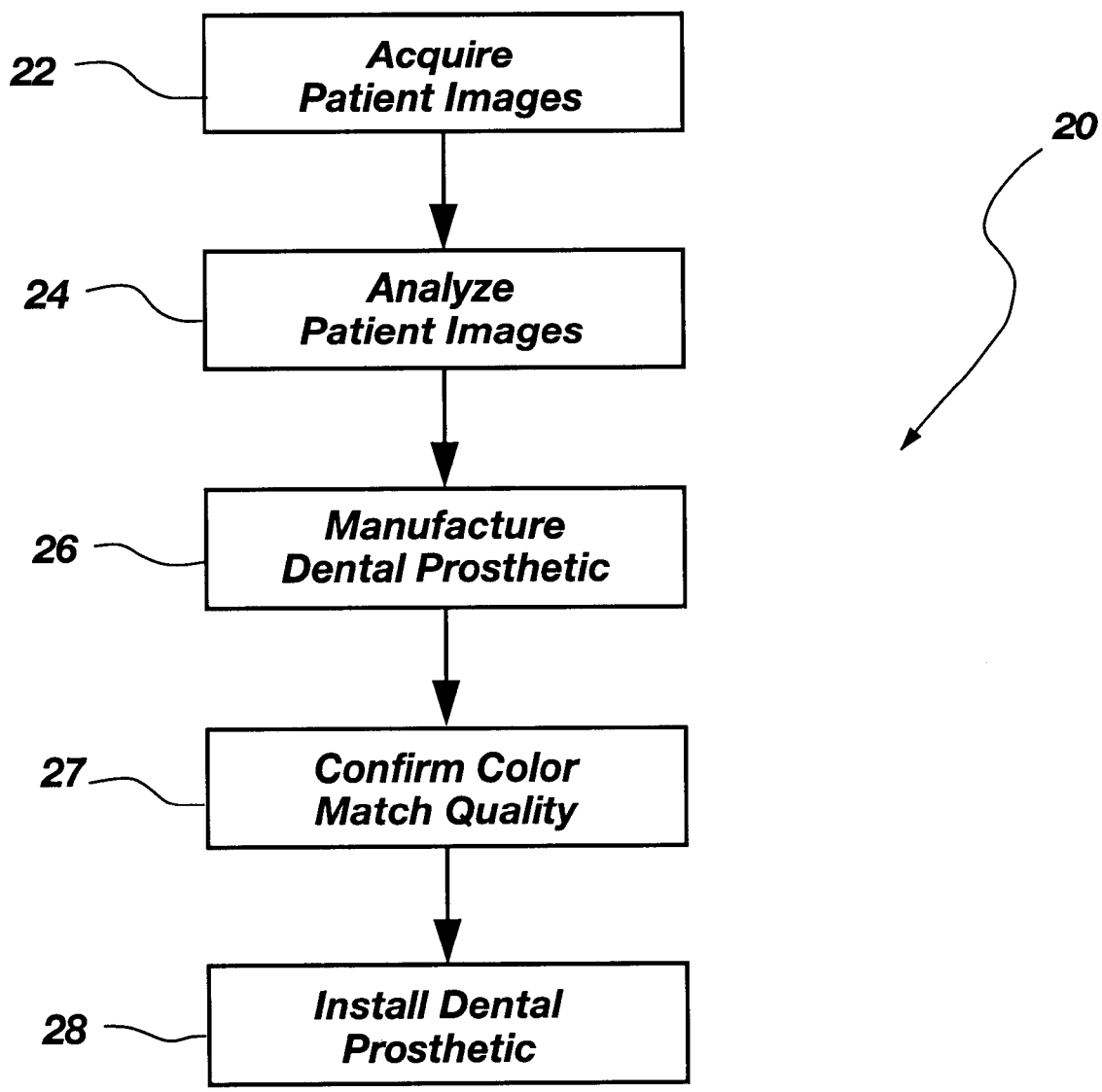
FIG. 2 is a flow diagram illustrating a method of prosthetic tooth manufacturing according to the invention.

Referring to FIG. 2, a method 20 for manufacturing a prosthetic tooth in accordance with the invention is disclosed. The method 20 includes acquiring patient images 22, analyzing patient images 24, manufacturing a dental prosthetic 26, optionally confirming color match quality 27 and installing the dental prosthetic 28. Each of these steps is further detailed below.

The method 20 begins with a dentist acquiring images 22 of a patient's natural teeth. The images 22 may be digital or analog. However, to facilitate image analysis, an analog image is first converted into a digital image. It should be noted that, although this invention will be described with respect to the manufacturing of a prosthetic tooth or teeth, those having skill in the technical field of this invention will understand that the invention is applicable to manufacturing a wide variety of other dental prosthetics including, for example, crowns, bridges, removable dentures and veneers. Further, the invention described herein may be used for restoring a patient's natural teeth when, for example, a tooth becomes broken, chipped or otherwise modified from its original condition, thereby requiring some form of restoration, such as bonding or filling. It will also be understood that while a dentist will typically acquire the patient images, others may do so instead, including, for example, a dental hygienist, assistant, or technician. Further, it will be understood that in some circumstances the "natural" teeth in the acquired images may actually include previously installed dental prosthetics. The terms "patient teeth image", "patient image" and "digital image" are used synonymously herein.

Figure 26:
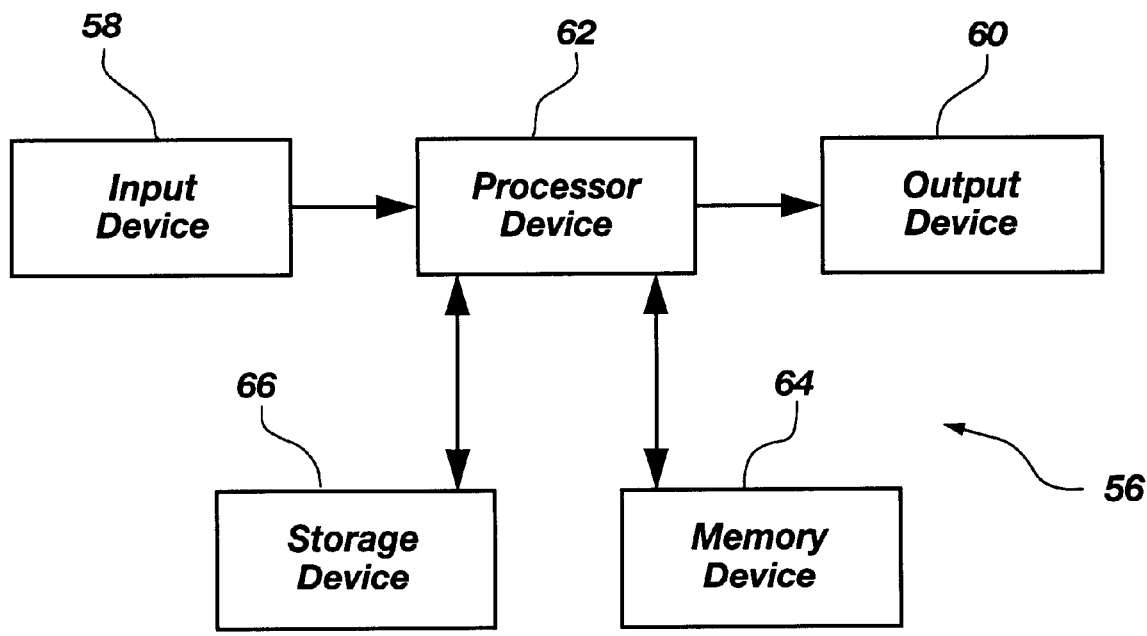
FIG. 26 is a block diagram illustrating an electronic system implementing the prosthetic tooth manufacturing method of the invention.

As shown in FIG. 26, the method 20 (as shown in FIG. 2) may be implemented in application software executing in an electronic system 56 including an input device 58, an output device 60, a processor device 62, a memory device 64 and a storage device 66. The application software is preferably Windows® 95 or Windows® 98 compatible. However, the application software may instead be compatible with any other operating system or environment including, for example, UNIX, LINUX, the Apple OS, Windows® NT, Windows® 3.x, and DOS. Also, the application software may include, or be compliant with, ActiveX controls or Java Applets. The application software may also operate in a computer network environment (not shown for clarity). The electronic system 56 preferably includes a processor device capable of running Microsoft® Windows® 98 operating system, for example but not limited to Intel® Pentium® and Advanced Micro Devices (AMD™), AMD-K6®-series processors. However, the electronic system 56 may include application software written to run on other processors running other operating systems.

Figure 3:
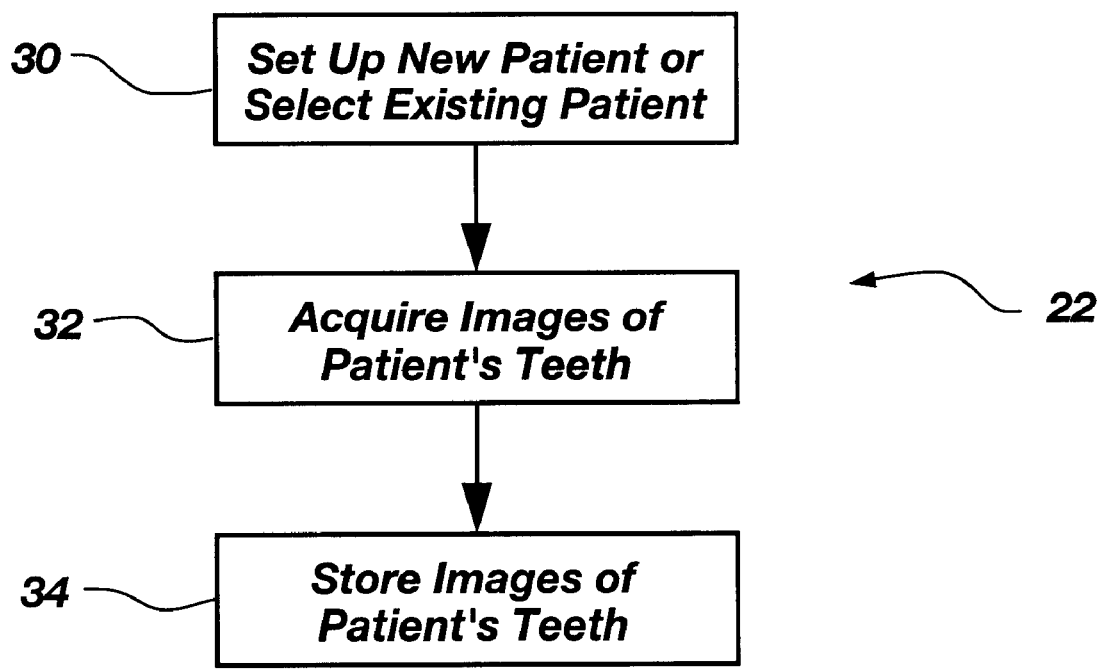
FIG. 3 is a flow diagram illustrating in more detail acquiring patient images 22 of the prosthetic tooth manufacturing method of FIG. 2.
Figure 4:
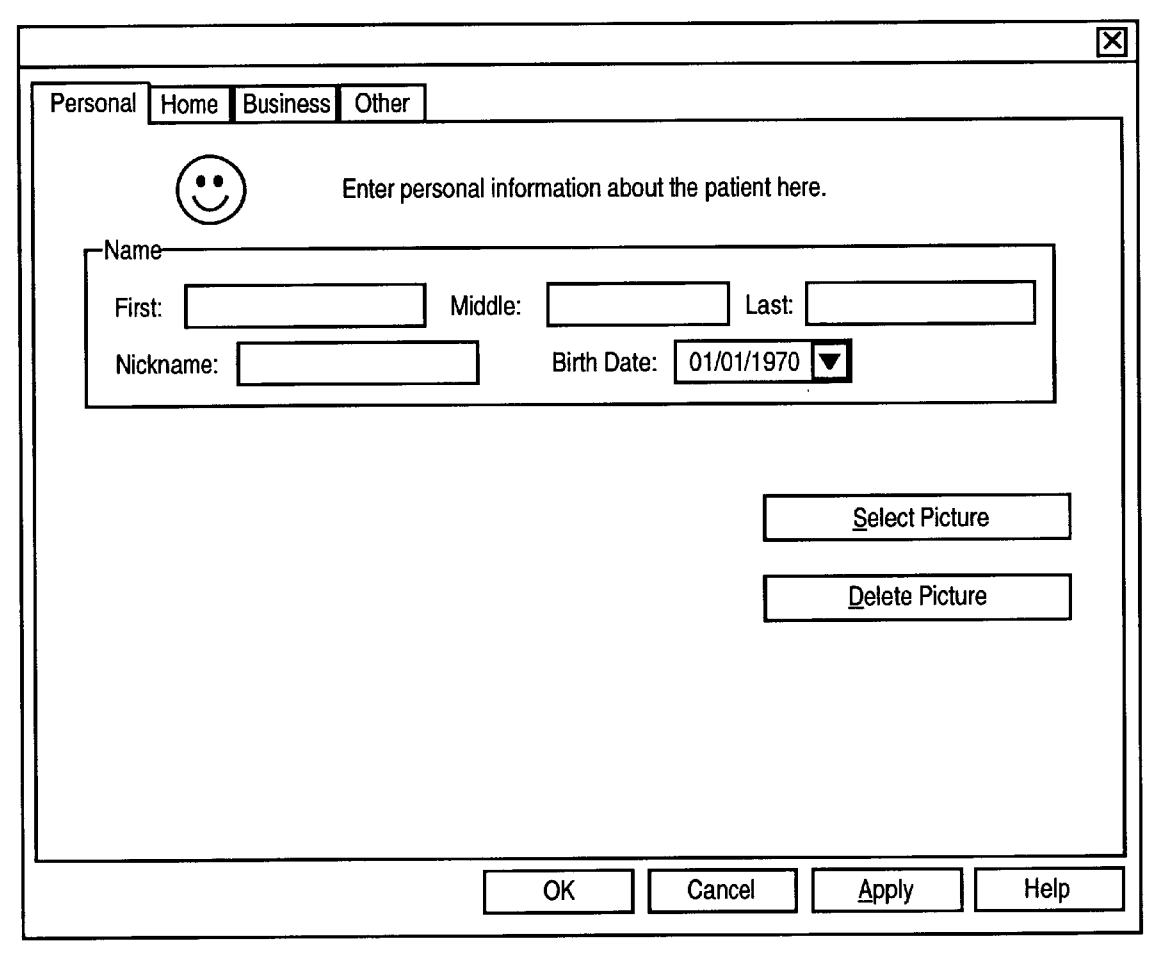
Figure 5:
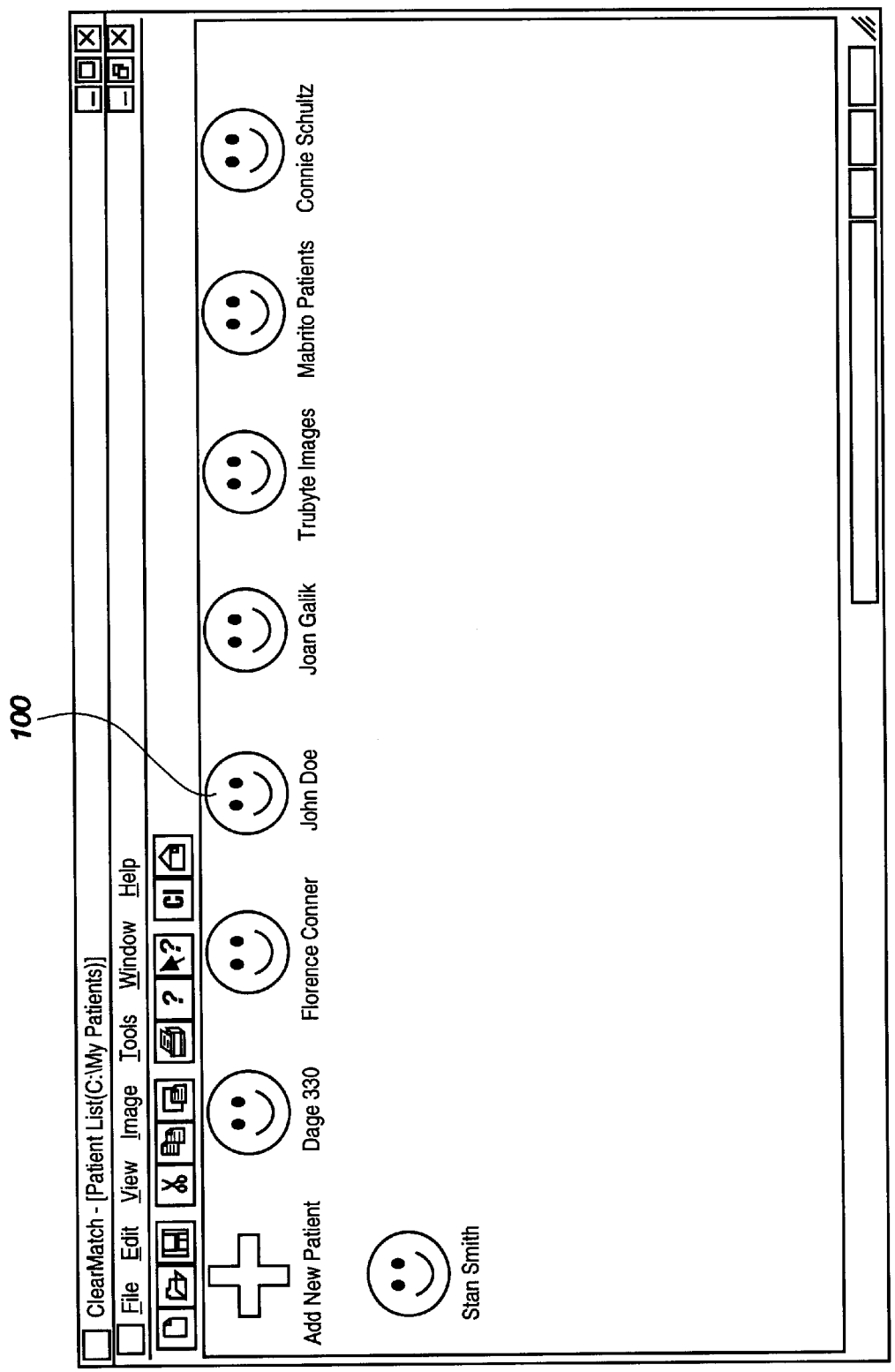
FIG. 5 is a screen capture illustrating selecting an existing patient 30 in accordance with FIG. 3.

Referring to FIG. 3, a flow diagram is shown illustrating in more detail the acquiring patient images step 22 of the prosthetic tooth manufacturing method of FIG. 2. In the preferred embodiment of the invention, images are organized by patient. The dentist may begin to acquire patient images by either setting up a new patient or selecting an existing patient 30. FIG. 4 illustrates a screen capture of a patient information screen with personal, home, business and other information that may be stored in the electronic system 56. FIG. 5 illustrates a screen capture of an embodiment of the step of selecting an existing patient 30, as shown in FIG. 3. As shown in FIG. 5, each patient may be represented by an icon 100. Once a patient has been selected, that patient's images may then be acquired if they have not already been stored in the electronic system 56.

Figure 6:
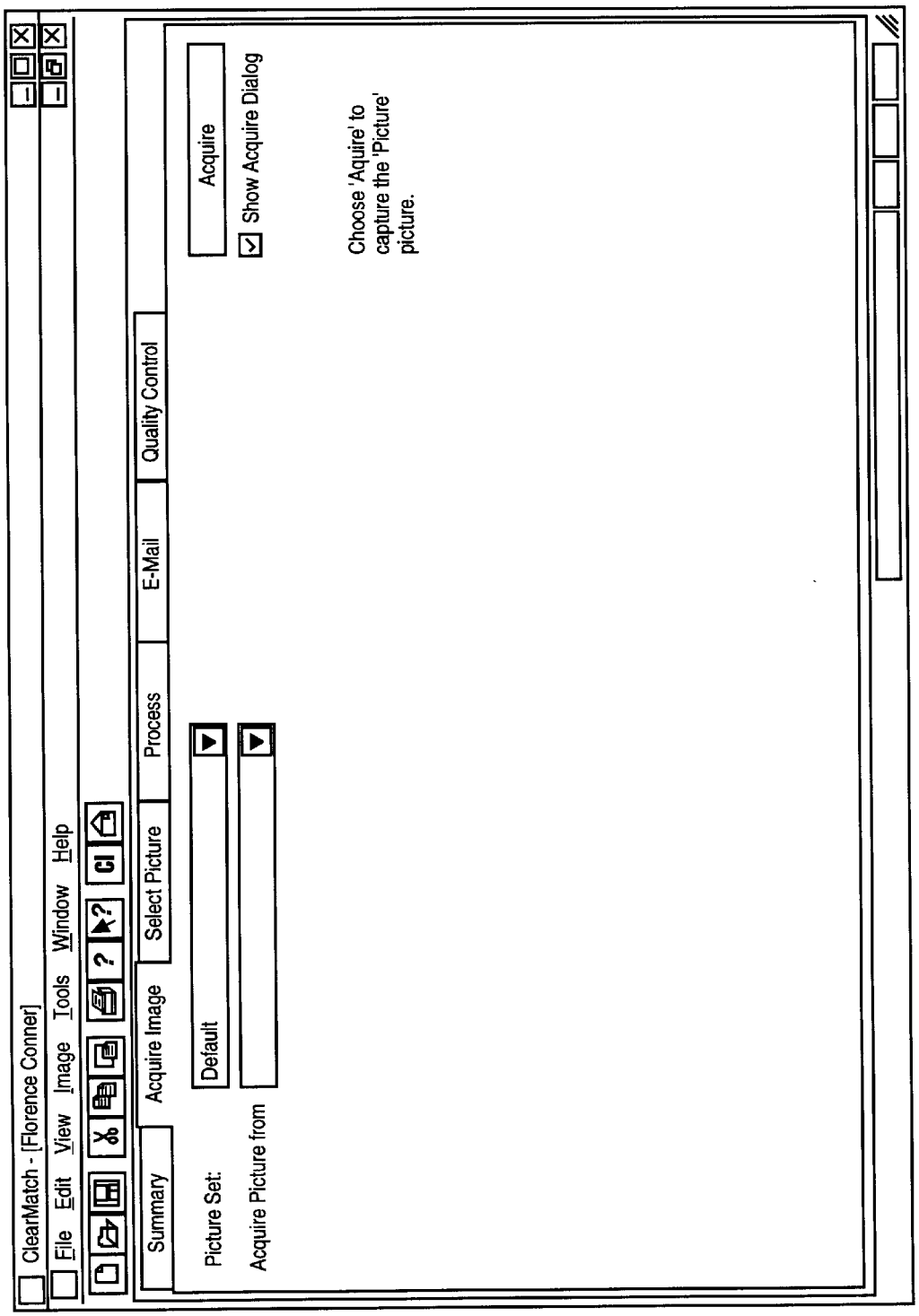
FIG. 6 is a screen capture illustrating image acquisition 32 as shown in FIG. 3.

Referring again to FIG. 3, a dentist acquires images of a patent's teeth 32. The images of interest may be the teeth adjacent to where a tooth is to be replaced. A dentist may acquire the patient teeth images using the input device 58, which may be any suitable device for acquiring digital images including, for example, a standard or intra-oral analog color charge coupled device (CCD) video camera providing a video feed to a TWAIN- compliant frame capture PC-card, a digital camera providing digital images directly to a 32-bit TWAIN driver through a Small Computer System Interface (SCSI) port, and a color image scanner scanning photographic slides, pictures, and the like and providing the resulting digital images directly to a 32-bit TWAIN driver through a SCSI port. The use of a SCSI port is exemplary only. The port interface could be Universal Serial Bus (USB), SCSI-II, IEEE-1394 (a high speed serial bus often referred to as "Fire Wire") or any other computer interface standard (whether serial or parallel) suitable for communicating large video or graphics files. FIG. 6 illustrates a preferred embodiment of the image acquisition step 32, showing a screen capture for image acquisition according to the method of FIG. 3. Software drivers for various digital cameras may be included in the electronic system 56 to allow a user to directly acquire patient images.

A computer-readable storage medium may be used to store the software previously described. A computer-readable storage medium may also be used to store digital images. As noted above, the patient images may have previously been acquired and stored on a computer-readable storage medium, for example, and not by way of limitation, a Jaz® or Zip® disc, a compact disc read-writeable (CD-RW) disc, a magneto-optic (MO) disk, CD-ROM disk, a DVD, a flash EEPROM card, a magnetic tape, or a ROM, PROM, EPROM, EEPROM, or flash EEPROM chip or any other computer data storage medium. In the case where the digital image to be analyzed is contained in a computer-readable storage medium, the dentist may "reacquire" them by transferring them from the storage medium to the electronic system 56. Storage device 66 may be a Jaz® or Zip® disk drive, and CD-RW drive or MO drive or any other type of mass storage device. Patient images may also be obtained from remote locations through the Internet or a modem connection to the electronic system 56. Thus, input device 58 may be a modem, or network interface card with an electrical connection to telephone lines or the Internet.

In order to reduce shade variation in the patient images due to the camera angle at which the images are taken, it is preferable, but not necessary, that the dentist use standardized camera angles. For example, the dentist may take standard left, right, and straight-on pictures level with the patient's mouth. Of course, other standardized angles are also possible or helpful, such as inferior and superior angles.

Also, in order to reduce variations due to camera type, film type, lighting conditions, etc., the dentist inserts reference tabs into the frame of the picture during image acquisition to provide references with respect to which the images may be normalized, as will be described in more detail below. These reference tabs include black and white references to calibrate the dynamic color range of the image. Many cameras have a nonlinear color range, thus calibrating with only black and white references may lead to color distortion within the dynamic color range of the image. For this reason, it is preferable to include at least one additional color standard in the frame of the picture. Preferrably, one or more suitable dental shade standards are placed in the frame of the picture to provide at least one color reference within the dynamic color range of the image. This "third" color reference compensates for any color range nonlinearity due to the particular camera being used to capture the image.

The black and white reference tabs are typically manufactured using homogeneous, non-reflective porcelains, and are intended to define the respective minimum and maximum Red, Green, and Blue (RGB) values for each image. However, the reference tabs may be manufactured with any materials, including inks and cloth, that represent the opposite ends (black and white) of the dynamic color range. Once the patient image is acquired, it is stored 34 (see FIG. 3). The patient image may be stored on the storage device 66 of the electronic system 56. It is contemplated that the black and white reference tabs may be included with one or more dental shade standard tabs on a card to be inserted in the picture frame during image acquisition. Such a card may be tailored to the particular dental shade standards being used to manufacture the dental prosthetic.

Referring once again to FIG. 2, after the patient images have been acquired, they are analyzed 24. The following detailed description will be described in the context of a dentist taking the pictures and installing the prosthetic tooth and a lab technician performing the image analysis and manufacturing the prosthetic tooth. Of course, it should be understood that other contexts are possible and within the scope of the invention. For example, the dentist might perform the image analysis and send the analyzed images to the dental technician, or the patient's images may be taken at the dental laboratory by the lab technician. Also, although the description herein implies a degree of physical distance between the dentist's office and the dental laboratory, the dentist and the laboratory may, in fact, reside in close physical proximity, including being located within the same offices. Thus, the dentist and the lab technician may use the same computer system if they are located in the same offices, thereby eliminating the need for the dentist to "send" the images to the lab technician.

The dentist may send the patient images to a dental laboratory for analysis using a wide variety of means including, for example and not by way of limitation, an e-mail or e-mail attachment, an Internet download, a modem-to-modem download, or physical delivery of a storage medium, such as a Jaz® or Zip® disc, or other portable data storage medium on which the images are stored.

Figure 7:
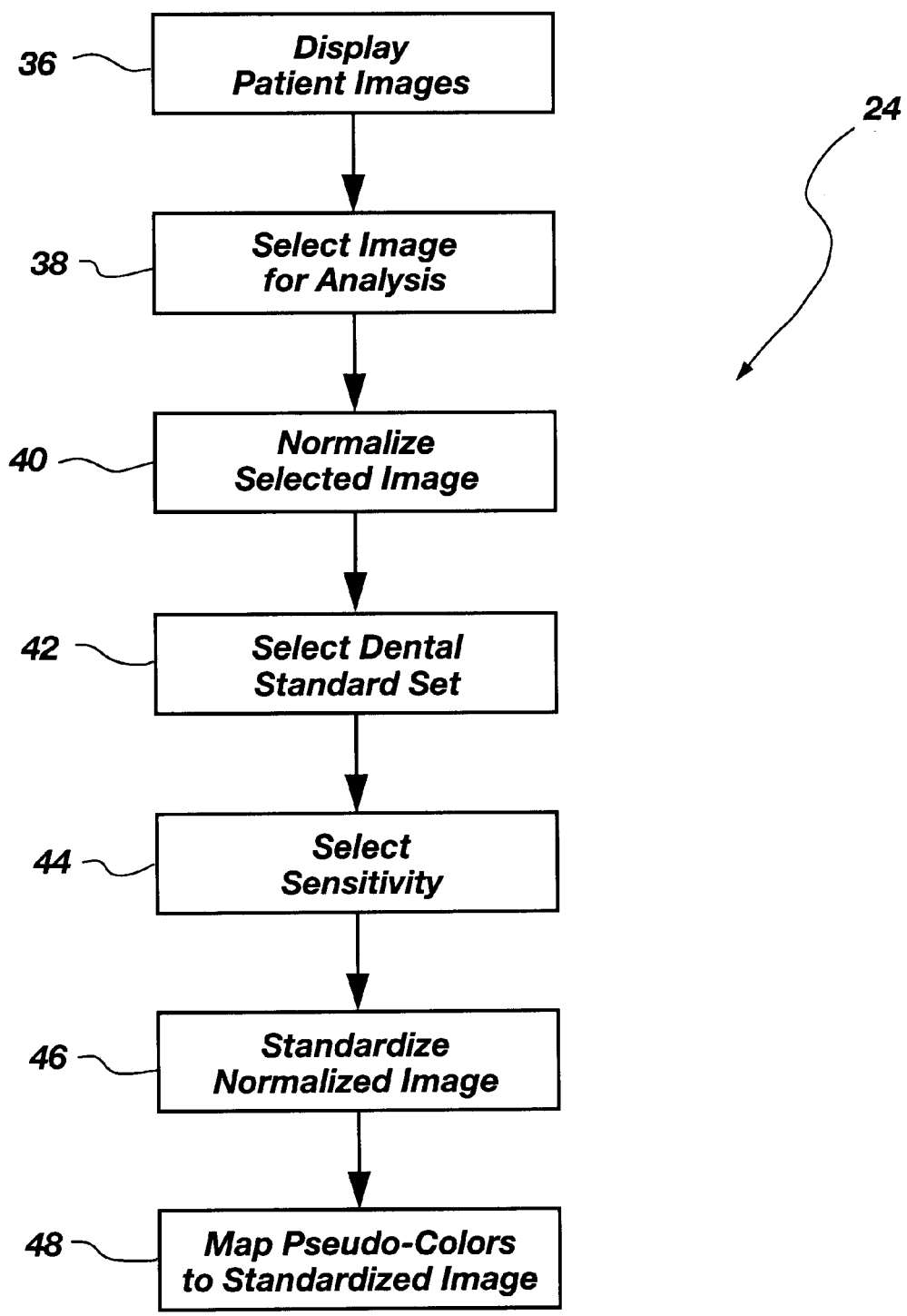
FIG. 7 is a flow diagram illustrating in more detail a patient image analysis procedure 24 of the prosthetic tooth manufacturing method of FIG. 2.

FIG. 7 is a flow diagram illustrating in more detail the patient image analysis procedure 24 of the prosthetic tooth manufacturing method of FIG. 2. Analyzing the patient images 24 includes displaying patient images 36, selecting an image for analysis 38, normalizing the selected image 40, selecting a dental shade standard set 42, selecting sensitivity 44, standardizing the normalized image 46 and mapping pseudo-colors to the standardized image 48.

Figure 24:
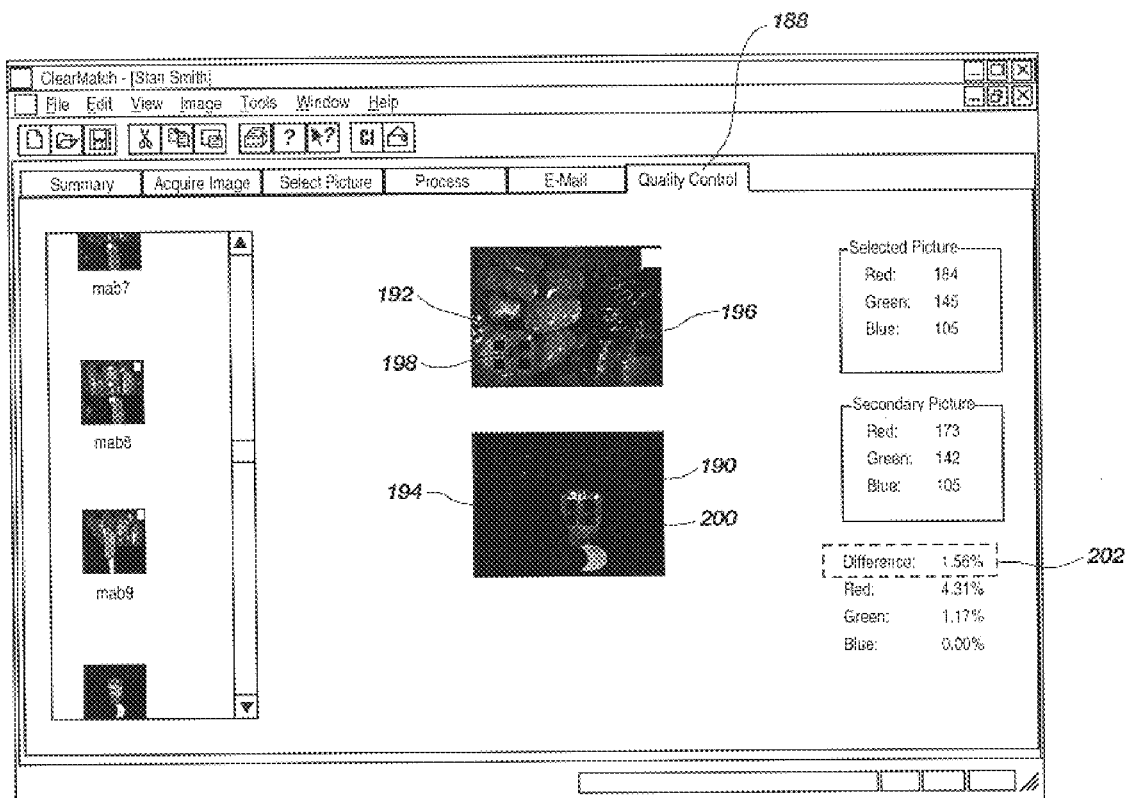
FIG. 24 is a screen capture illustrating an optional quality analysis step 27 which may follow the prosthetic tooth manufacturing step 26 of FIG. 2.

Upon receiving the patient images, the lab technician analyzes the images using an electronic system 56 (FIG. 24) preferably adapted with software for his or her use in implementing the method 20. As described herein, the dentist and the lab technician have nearly identical application software executing on their respective electronic systems 56 (FIG. 24). However, it will be understood that certain functions desirable in the lab technician's software (e.g., image analysis) may not be necessary in the dentist's software (and therefore may not be present therein), and vice-versa.

Figure 8:
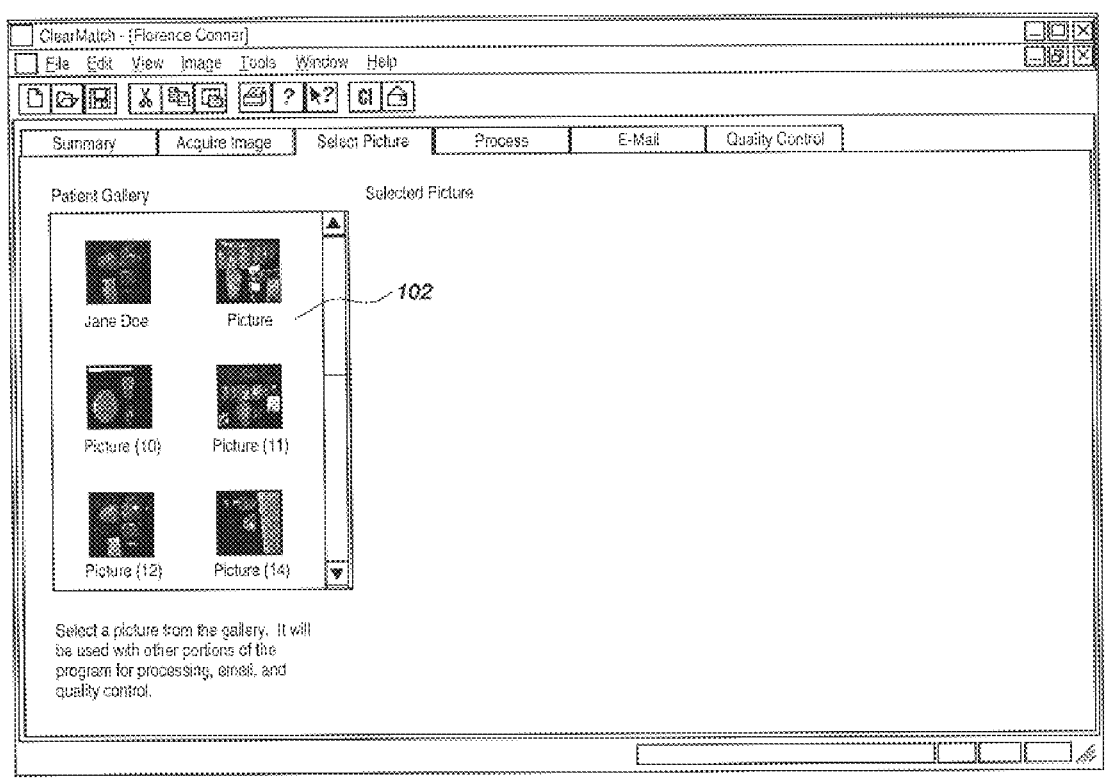
FIG. 8 is a screen capture illustrating the display patient images step 36 and the select image for analysis step 38 in accordance with the detailed patient image analysis procedure of FIG. 7.
Figure 9:
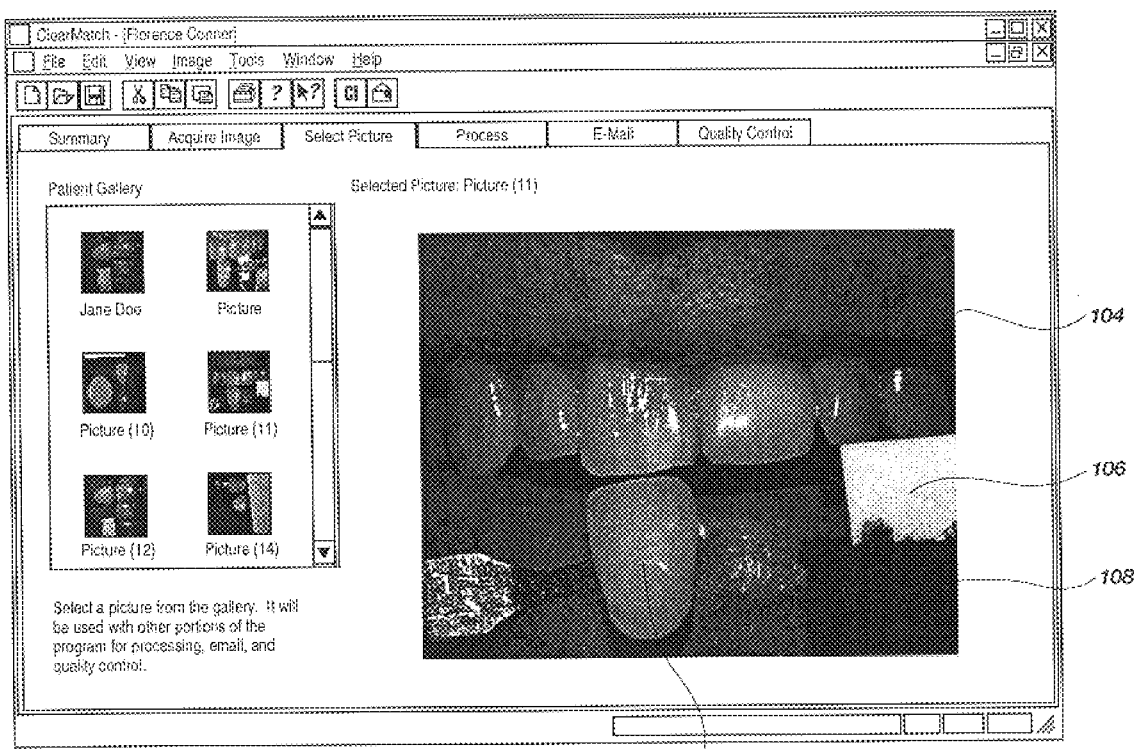
FIG. 9 is a screen capture illustrating a selected picture 38 of the detailed patient image analysis procedure 24 of FIG. 7.
Figure 10:
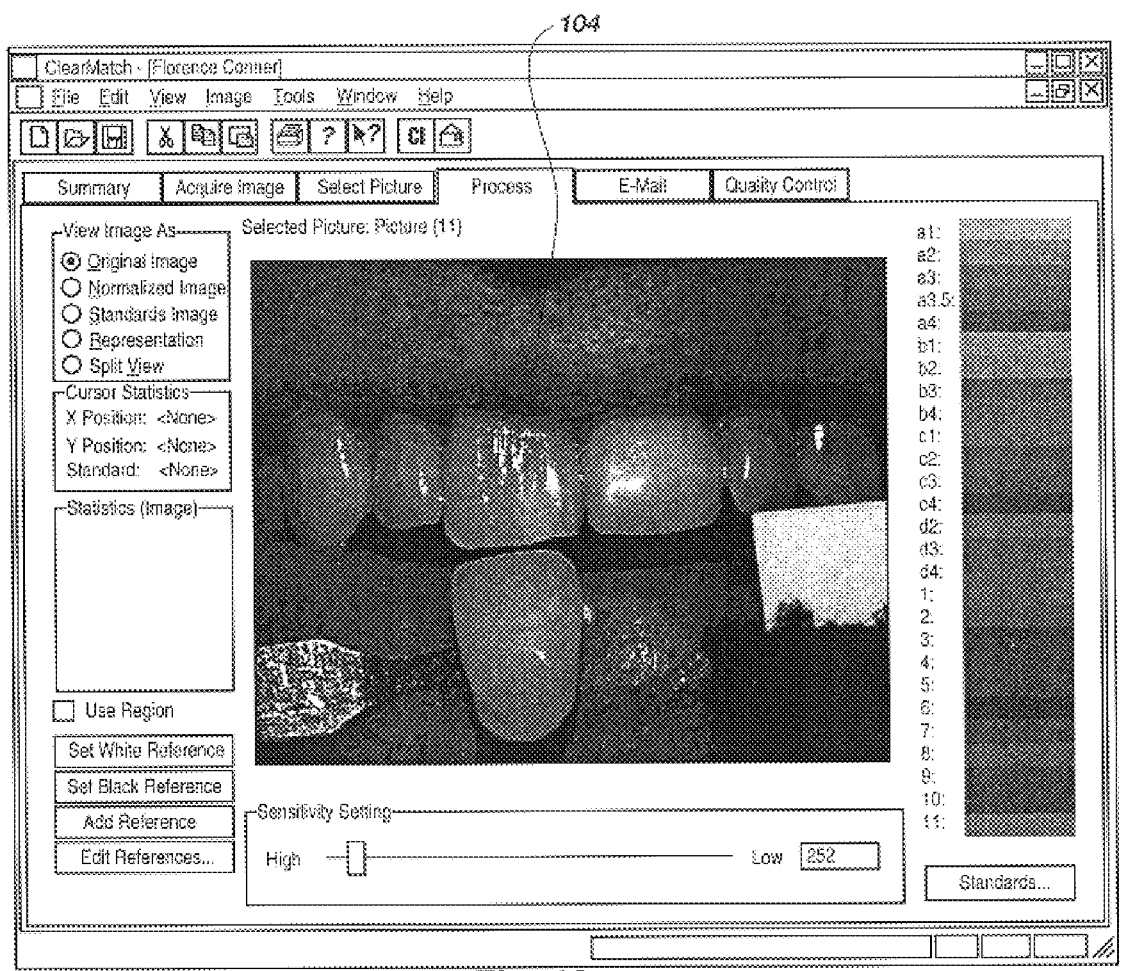
FIG. 10 is a screen capture illustrating the original image of the picture selected in FIG. 9.

As shown in FIG. 8, the lab technician begins analysis of the images by displaying the patient images 36 in a thumbnail gallery 102. The lab technician then selects 38 one of the images from the gallery 102 for analysis, and displays the selected image 104 in large format, as shown in FIG. 9. Prior to image processing, the "selected image " 104 may also be referred to herein as the "original image" 104. FIG. 9 also illustrates a white reference tab 106, a black reference tab 108 and an "A1" dental shade tab 109 used to normalize 40 the selected image 104. Referring to FIG. 7, the lab technician continues the image analysis procedure 24 by normalizing 40 the selected image 104. FIG. 10 illustrates a screen capture of the original image 104 prior to normalization.

Figure 11:
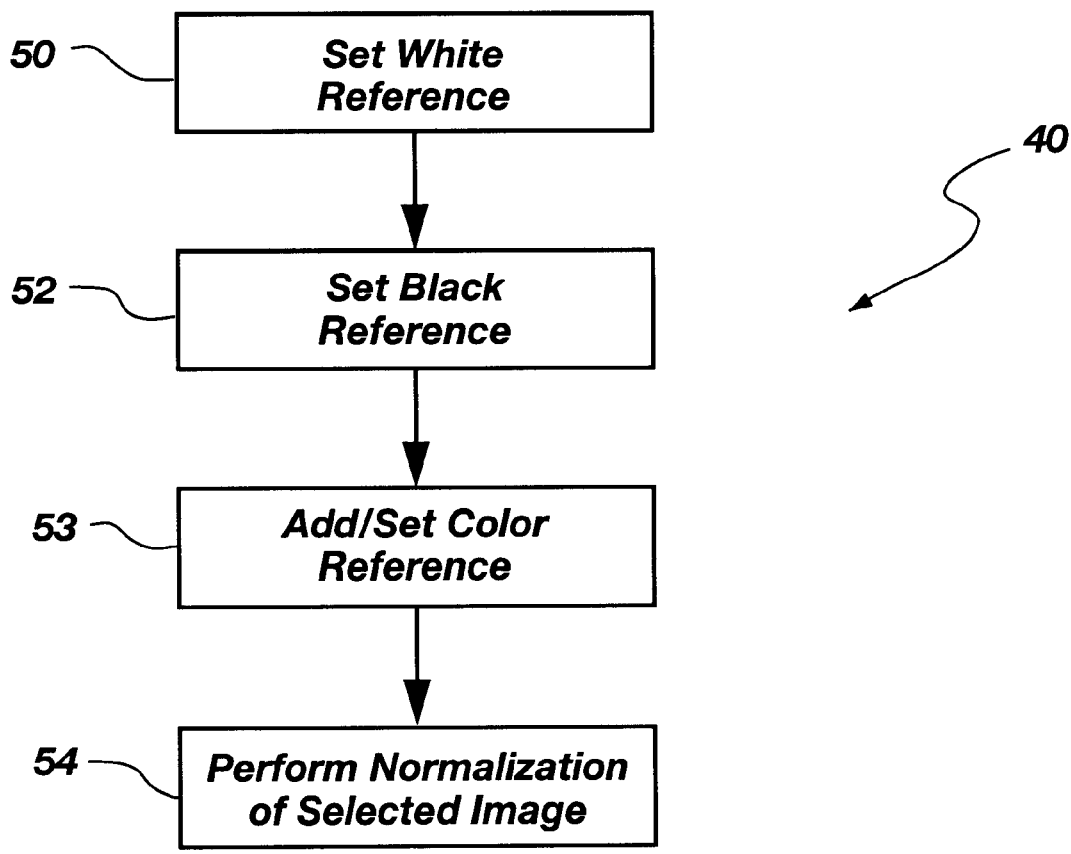
FIG. 11 is a flow diagram illustrating in more detail the normalize selected image step 40 of FIG. 7.
Figure 12:
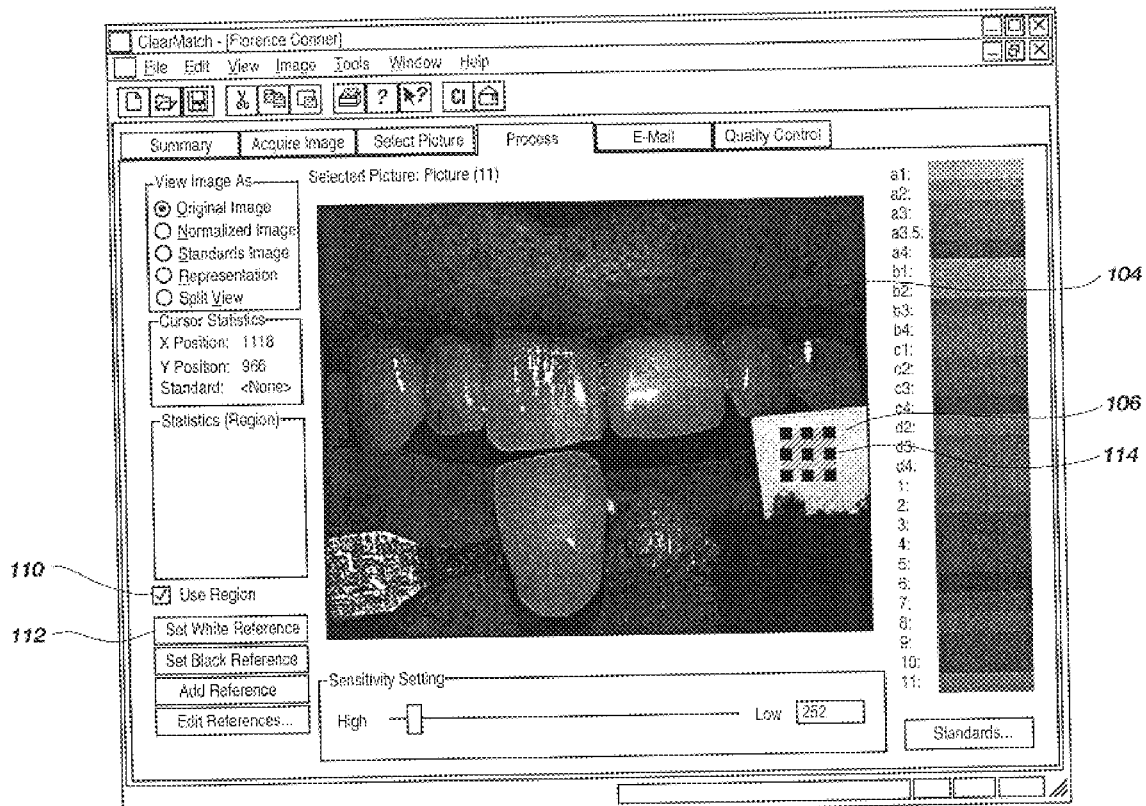
FIG. 12 is a screen capture illustrating the set white reference step 50 of FIG. 11.

FIG. 11 is a flow diagram illustrating in more detail the normalize selected image step 40 of FIG. 7. The normalization process 40 includes setting a white reference 50, setting a black reference 52, adding at least one color reference 53 and performing the normalization 54. To illustrate the preferred embodiment of the normalization process 40, refer also to FIG. 12. The preferred embodiment of the normalization process allows the user to select whether a user definable region will be used or whether a point will be used when selecting the white and/or black references. As shown in FIG. 12, that option is embodied in a "Use Region" check box 110. The terms "user definable region" and "selection area" will be used interchangeably herein. Additionally, the white, black and color references may be generally referred to as "normalization references." The following illustrations of the preferred embodiment will assume that the "Use Region" check box 110 has been selected.

The lab technician begins the normalization process 40 by selecting a "Set White Reference" button 112 which generates a rectangular, size adjustable and movable selection area 114. The lab technician then optionally adjusts the size of the selection area 114 and moves the selection area 114 so that it is placed on a white reference tab 106 previously inserted into the original selected image 104 by the dentist. The lab technician may then set a black reference 52 using a similar procedure.

Figure 13:
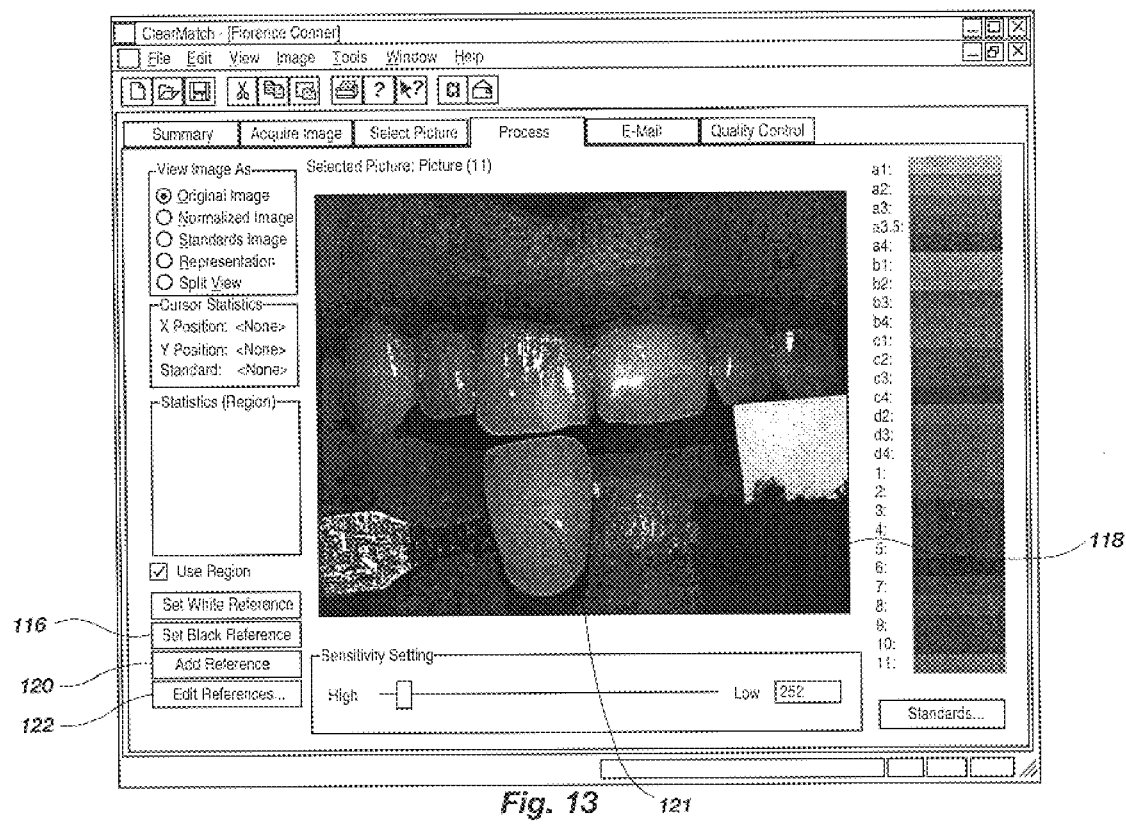
FIG. 13 is a screen capture illustrating the set black reference step 52 of FIG. 11.

Referring to FIG. 13, the lab technician selects a "Set Black Reference" button 116 which again generates a selection area. The lab technician then optionally adjusts the size of the selection area and moves the selection area to that it is placed over a black reference tab 118. The selection area is not shown in FIG. 13 because it has been placed over the black reference tab 118, since the selection area and black reference tab 118 are both black. The lab technician may then set one or more color references 53.

To add a color reference, the lab technician selects an "Add Reference" button 120 which again generates a selection area that is placed over a selected region, in this example, on the "a1" dental tooth shade guide 121, see FIG. 13. Additional color references may be added to the normalization references used to normalize the image by repeating the add reference procedure 53 just described.

Figure 14:
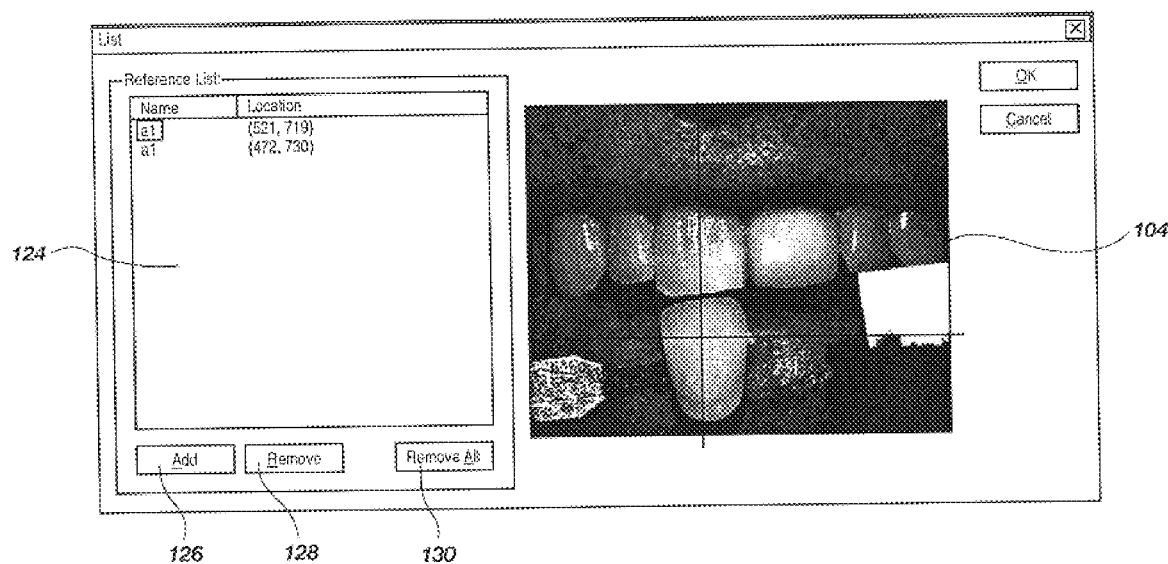
FIG. 14 is a screen capture illustrating the add/set color reference step 53 of FIG. 11.

Additionally, the color references may be removed or replaced by the technician selecting the "Edit References . . ." button 122. FIG. 14 illustrates a screen capture of a window for adding and removing color references in accordance with the preferred embodiment of the invention. The left side 124 of the screen capture window lists the existing color references that have been added, here there are two such "a1" color references. The right side of the screen capture window illustrates the selected image 104 with "cross-hairs" indicating the exact location on the image of the highlighted color reference. The lab technician may add and remove color references from this window. To add an additional color reference, the lab technician selects the "Add" button 126 and follows a procedure identical to that outlined above. To remove a color reference, the lab technician highlights the undesired color reference and selects the "Remove" button 128. Alternatively, the lab technician may "start from scratch" by removing all color references by selecting the "Remove All" button 130.

Of course, the order of setting the references (i.e., white reference 50, black reference 52 and color reference 53) may be performed in any order. Normalization 40 may be performed with only the black and white normalization references. However, the addition of at least one color reference to the black and white normalization references is preferred because the dynamic color range of many color cameras is nonlinear.

Figure 15:
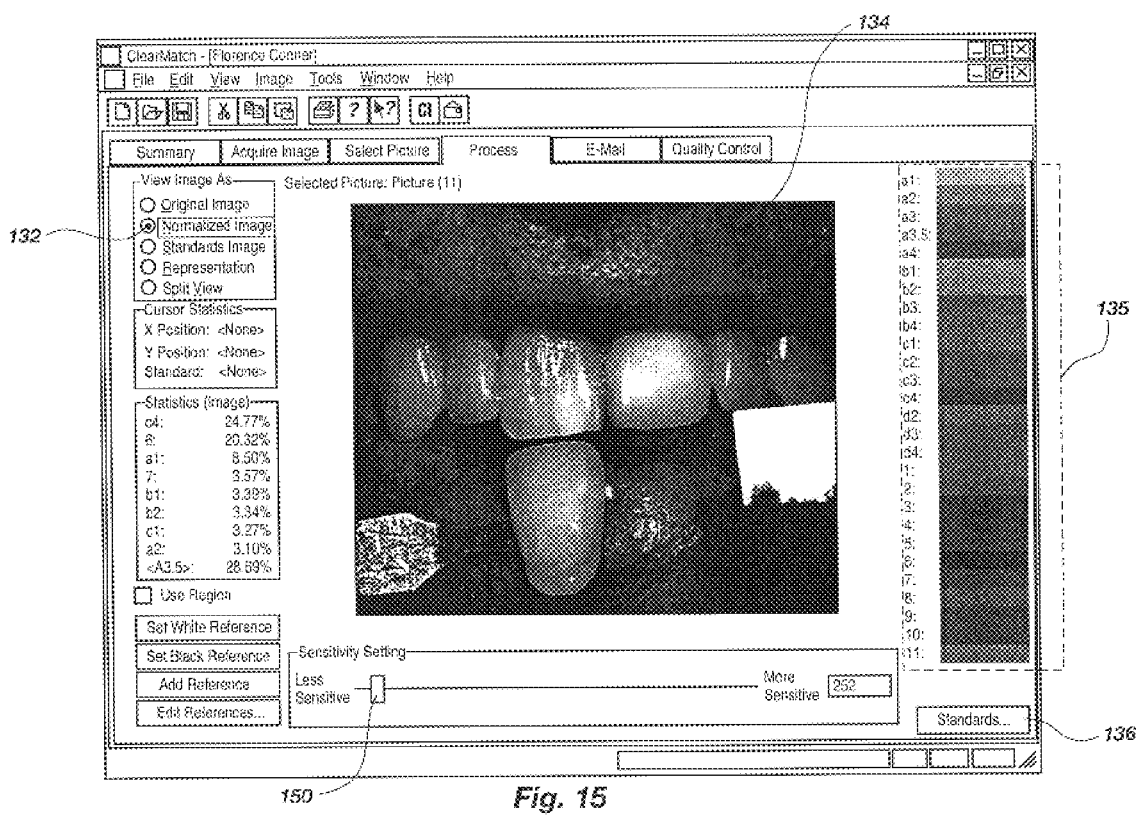
FIG. 15 is a screen capture illustrating the perform normalization of selected image step 54 of FIG. 1 and the resulting normalized image step 40 of FIG. 7.

Once the desired normalization references (black, white and at least one color reference) are set, the lab technician performs the normalization step 40 by selecting the "normalized image" view 132, see FIG. 15. The software in the electronic system 56 automatically computes and displays a normalized image based on the normalization references. The normalization step 40 may produce a normalized look-up table to convert each pixel in the original image to a normalized image. An example follows to explain this aspect of the disclosure. Assume, for the moment, that the system is using the RGB color model and that each pixel of the selected image 104 is stored as an 8-bit index into a 256 color look-up table such as the following:

TABLE 1

| Index | Red | Green | Blue |
|---|---|---|---|
| 00000000 | 00000010 | 00000101 | 00000001 |
| 00000001 | 00000100 | 00000110 | 00000011 |
| 00000010 | 00000101 | 00000111 | 00000101 |
| . . . | . . . | . . . | . . . |
| 11111110 | 11110110 | 11111101 | 11111100 |
| 11111111 | 11111001 | 11111110 | 11111111 |

Under this circumstance, the software normalizes the look-up table by recalculating the red, green, and blue values for each index. The calculations are as follows:

$$\text{NewRedValue} = \left(\frac{255}{\text{RedRange}}\right)(\text{Index} - \text{BlackRef.RedValue}) + 0.5 \quad (1)$$

$$\text{NewGreenValue} = \quad (2)$$
$$\left(\frac{255}{\text{GreenRange}}\right)(\text{Index} - \text{BlackRef.GreenValue}) + 0.5$$

$$\text{NewBlueValue} = \left(\frac{255}{\text{BlueRange}}\right)(\text{Index} - \text{BlackRef.BlueValue}) + 0.5 \quad (3)$$

where,

Red Range=White Reference Red Value−Black Reference Red Value (4)

Green Range=White Reference Green Value−Black Reference Green Value (5)

Blue Range=White Reference Blue Value−Black Reference Blue Value (6)

Of course, images that directly store the red, green and blue values for each pixel (e.g., so-called "24-bit" images), that do not use a look-up table, may be normalized in much the same way, except that the normalization procedure is performed on the pixel values of the image itself rather than on the values in a look-up table. Continuing with the example described above, once the look-up table for the selected image 104 is normalized, the selected image 104 is redisplayed as a normalized image 134, as shown in FIG. 15, using the normalized look-up table.

Figure 16:
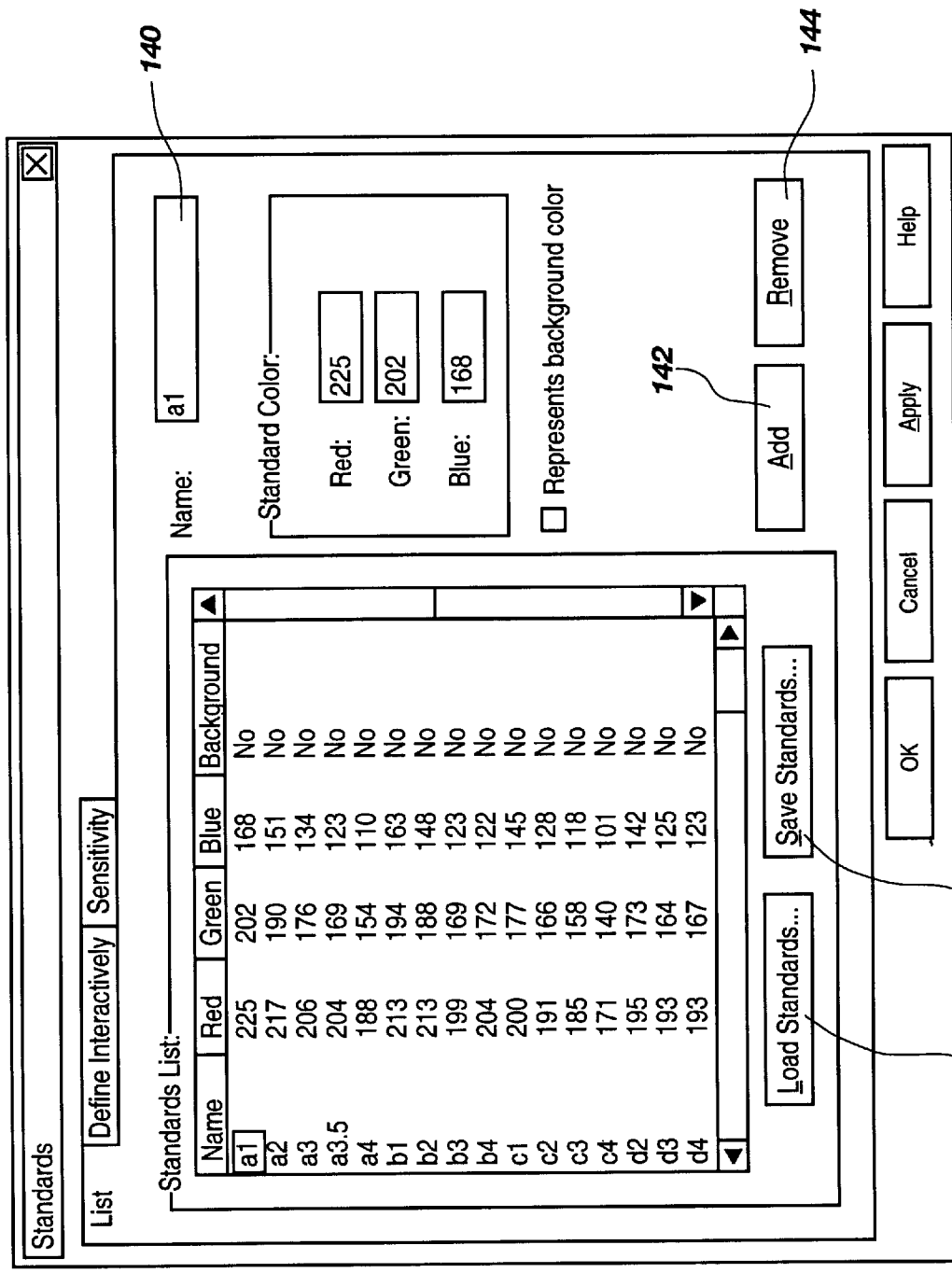
FIG. 16 is a screen capture illustrating the select dental shade standard set step 42 of FIG. 7.

Referring to FIGS. 7 and 15, once a normalized image 134 is obtained, the lab technician may then select the desired shade standard set 42 to be used in manufacturing the prosthetic tooth. As shown in FIG. 15, the currently selected dental shade standard set 135 appears on the right (in the dashed box). In the preferred embodiment of the invention, shade standard sets are selected using a "Standards . . . " button 136. Selecting the "Standards . . ." button 136 brings up a select dental standards window to allow the user to select or edit predefined dental shade standard sets. FIG. 16 is a screen capture illustrating the select dental standard set step 42 of FIG. 7. The user may load predefined dental shade standard sets by selecting the "Load Standards" button 138. Alternatively, the user may add and remove individual dental shade standards from an existing predefined dental shade standard set. According to the preferred embodiment a user may add a dental shade standard by typing a new dental shade standard name in a window 140 and optionally adjust the RGB color of that new standard and then selects the "Add" button 142 which adds the new color (dental shade standard) to the current dental shade standard set. To remove an individual dental shade standard from a dental shade standard set, the user highlights the undesired color standard from the "Standards List" and selects the "Remove" button 144. Once a dental shade standard set has been edited, the user may save it under a new name by selecting a "Save Standards . . . " button 145.

Figure 17:
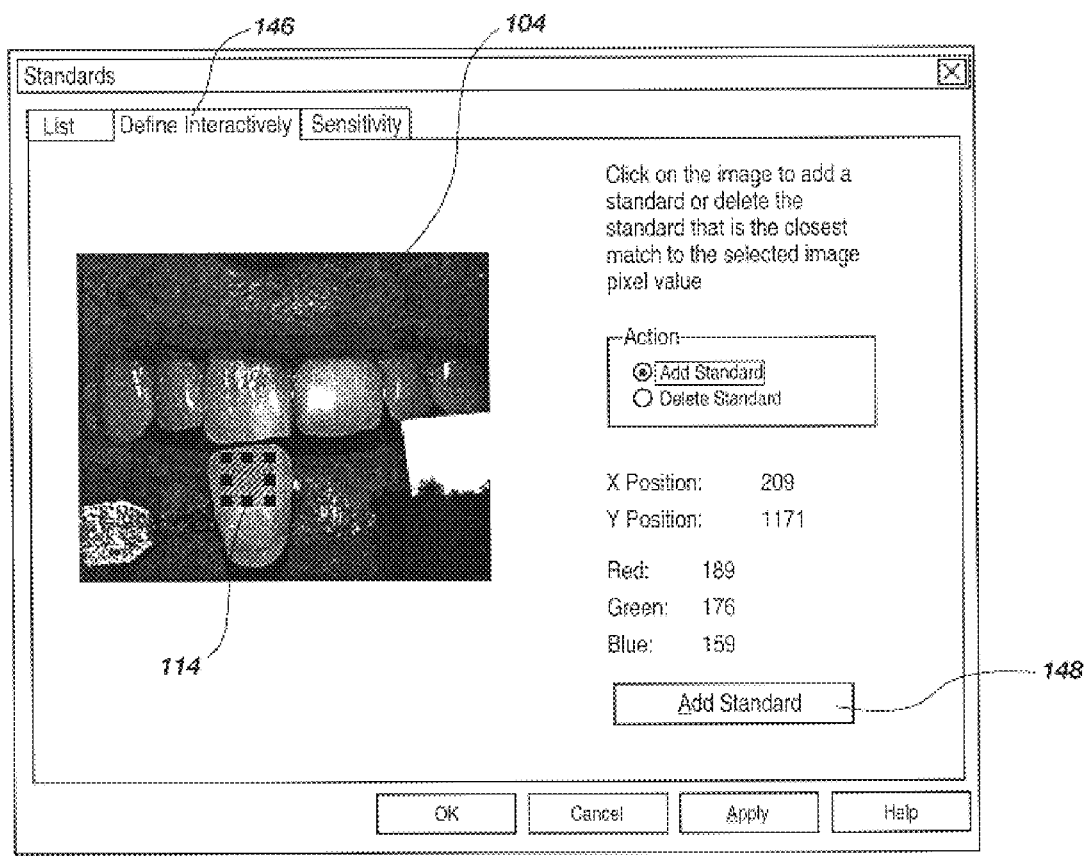
FIG. 17 is a screen capture illustrating means for interactively defining a dental shade standard.

In yet another embodiment, dental shade standards may be interactively defined. Referring to FIG. 17, a screen capture illustrating a window for interactively defining dental shade standards is shown. Dental shade standards may be defined and saved based on a user definable region placed over a known color shade standard within the selected image 104. For example in FIG. 17, the lab technician may add an "a1" dental shade standard by selecting the "Define Interactively" tab 146, moving and adjusting the size of a user-definable selection area 114 and placing it over the "a1" dental shade guide in the selected image 104, then selecting an "Add Standard" button 148. The software automatically calculates the average RGB color content in the user-definable selection area 114 and adds the new dental shade standard to the current dental shade standard set. Using a similar procedure, dental shade standards may be removed.

Although the shade standards can be generated from images of the conventional shade guides previously described, it is preferable that the shade standards be generated from flat, non-reflective, homogeneous porcelain samples. This is because the conventional shade guides are manufactured to look like a conventional tooth, and thus, are curved, semi-glossy and non-homogeneous in the porcelain shade they represent. Thus, for example, a conventional shade standard "a1" shade tab is made to look like a tooth, so it is curved, semi-glossy, and is only a true "a1" porcelain when viewed at its center and in a region without reflection. The preferred flat, non-reflective, homogeneous porcelain samples are better adapted to provide accurate shade standards for digital image analysis.

While generally opaque in appearance, the thinner regions of a tooth (e.g., the incisal region of a cutting tooth, thin layers of tooth enamel, etc.) may actually be translucent. The translucent appearance of a tooth may include varying shades of gray, blue, orange and amber. Thus, the methods, apparatuses and systems of the invention may include "incisal tooth shade standards" in addition to standards generated from conventional shade guides or shade standards generated from flat, non-reflective, homogeneous porcelain samples. The term "shade standard set" as used herein may include incisal tooth shade standards.

Selecting a standardization sensitivity 44 may be performed at any time. For convenience it is shown as occurring after the selecting sensitivity 44 step in FIG. 7. In the preferred embodiment, the lab technician selects a standardization sensitivity level using a sensitivity selector 150, and the software then attempts to match each pixel in the normalized image 134 (FIG. 15) to one of the selected dental shade standards. To accomplish this for each pixel, the software calculates a distance, D, between the RGB values of the pixel and the RGB values of each of the selected standards, according to the following equation:

$$D=(R_P-R_S)^2+(G_P-G_S)^2+(B_P-B_S)^2 \qquad (7)$$

where $R_P$, $G_P$, $B_P$ are the red, green and blue values of the pixel, respectively, and $R_S$, $G_S$ and $B_S$ are the red, green and blue values of a given standard, respectively. The software then determines the standard having the minimum distance calculated. If this minimum distance does not exceed the sensitivity level (e.g., 4,000) set by the lab technician, the software assigns the standard color associated with the minimum distance to the pixel. If, instead, the software determines that the minimum distance calculated exceeds the sensitivity level selected, then the software assigns the color black to the pixel.

Figure 18:
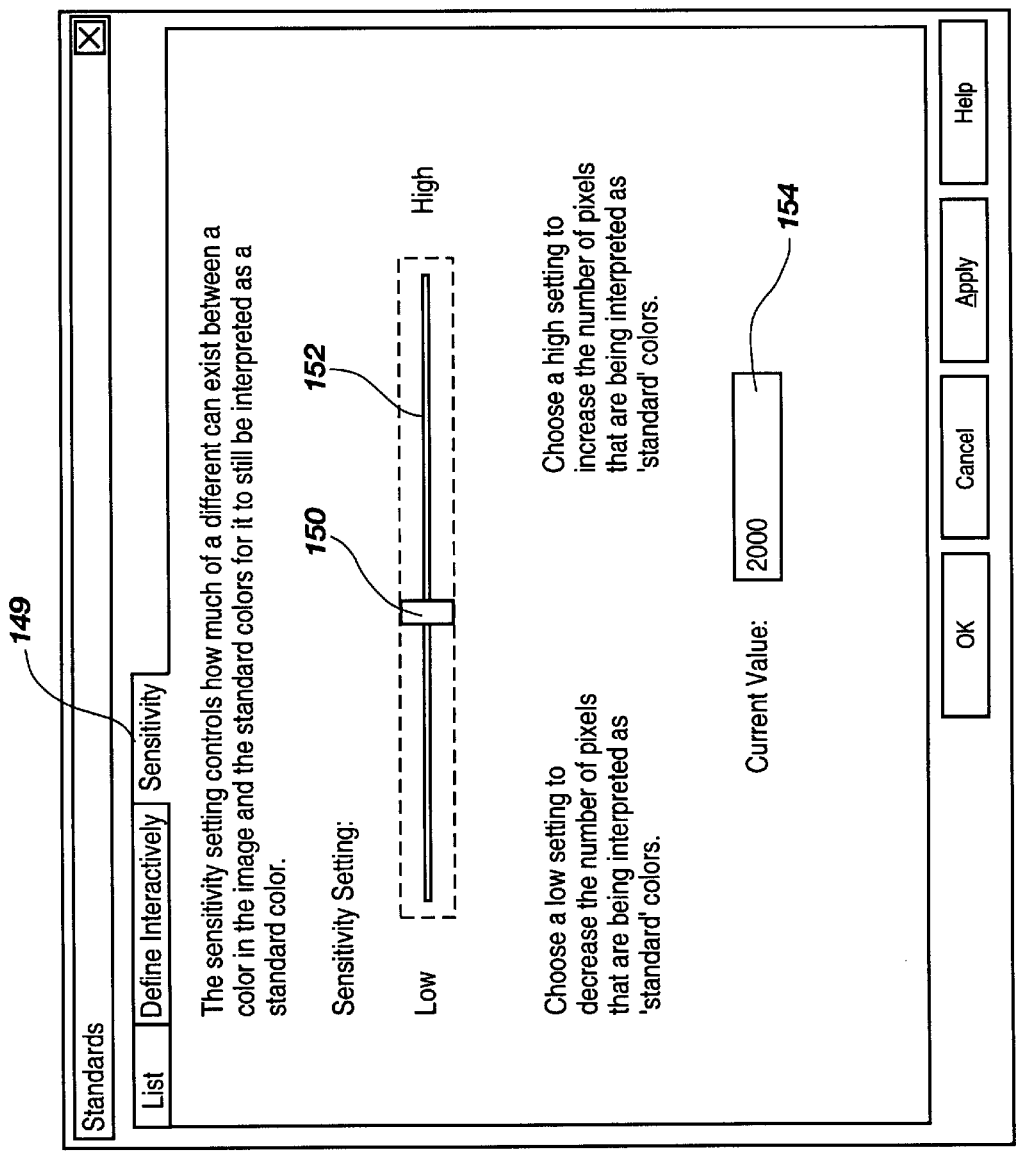
FIG. 18 is a screen capture illustrating one embodiment of the select sensitivity step 44 of FIG. 7.

Sensitivity may also be adjusted when the user selects and edits dental shade standards. Referring to FIG. 18, a screen capture illustrating means for adjusting sensitivity is shown. In FIG. 18, the user selects the "Sensitivity" tab 149 and adjusts a sensitivity selector 150 along a slider bar 152 to allow adjustment from 0 to 4000. Adjustment may be accomplished by dragging the sensitivity selector 150 along the slider bar 152 with a pointing device such as a mouse. Alternatively, the desired sensitivity may be entered directly through the "Current Value" window 154. While the fine adjustment available through the sensitivity selector 150 is considered the preferred embodiment, other arrangements are also contemplated within the scope of the invention. For example, an alternative embodiment may have three radio buttons for the user to select between low, medium and high sensitivity.

Figure 19:
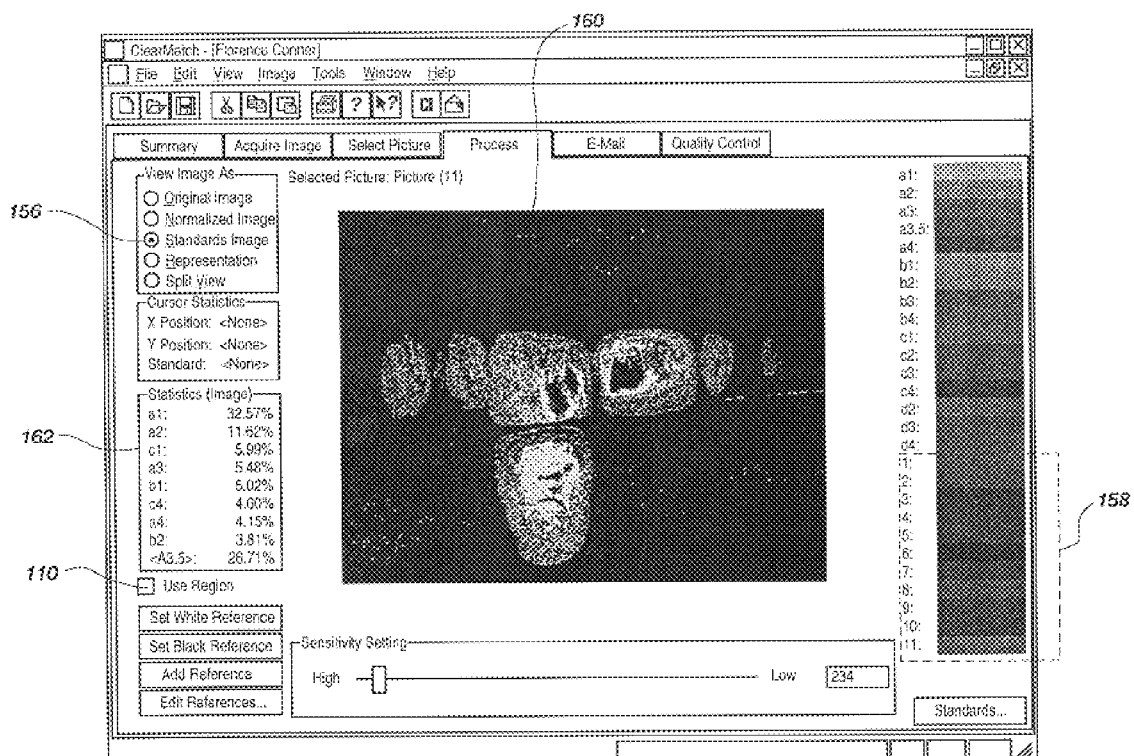
FIG. 19 is a screen capture illustrating a standardized image 46 of FIG. 7 with high sensitivity.

The standardize normalized image step 46 of FIG. 7 is performed automatically when the "Standards Image" view 156 is selected, see FIG. 19, and is recalculated automatically when the sensitivity is adjusted thereafter. Alternative embodiments may include the option of calculating the standardized image only when commanded to do so. FIG. 19 illustrates a screen capture of a standardized image 160 with a relatively high sensitivity. The standardized image 160 in FIG. 19 shows the dental shade standard colors assigned to each pixel. As noted above, black indicates a pixel color outside the sensitivity setting (ie., the distance, D, exceeds 234, as shown in FIG. 19). The colors assigned may include incisal tooth shades if a dental shade standard set including incisal tooth shades was selected. In FIG. 19, dental tooth shade standards 1–11 are incisal tooth shades (see dashed box 158).

Figure 20:
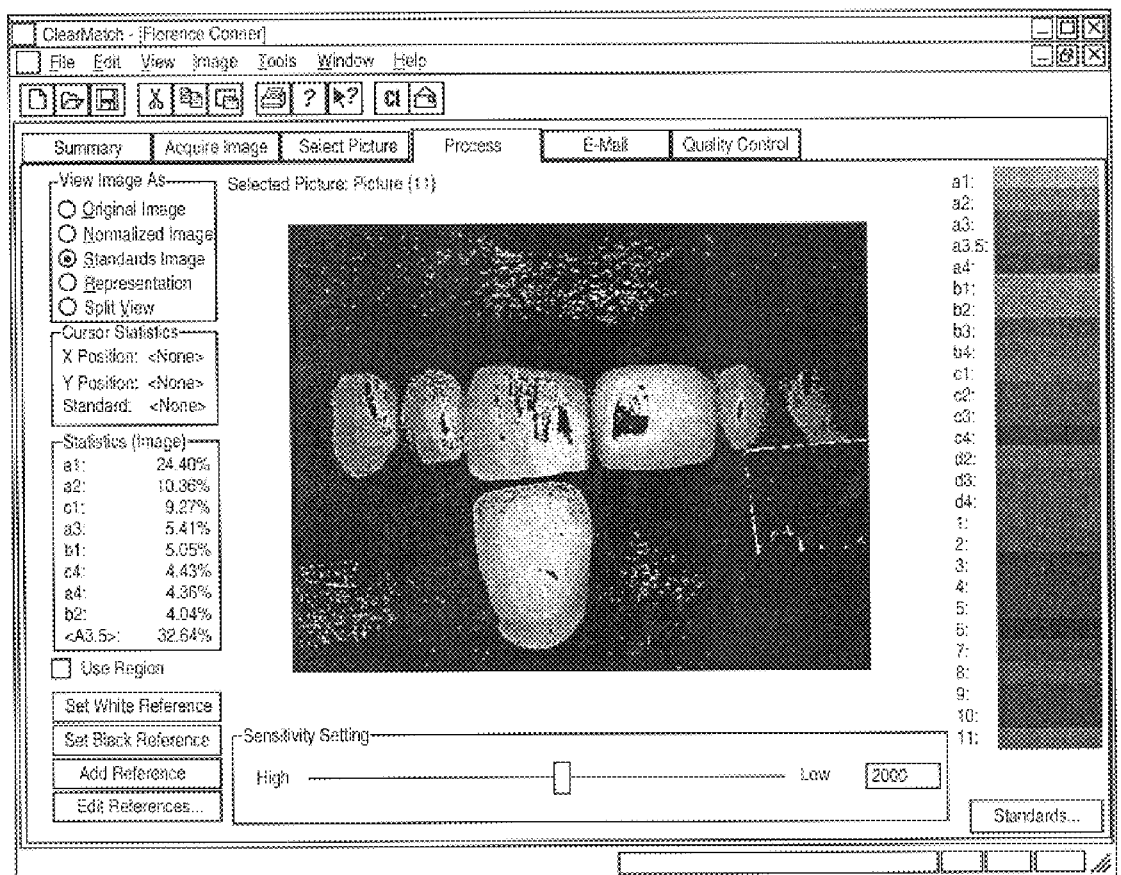
FIG. 20 is a screen capture illustrating a standardized image 46 of FIG. 7 with medium sensitivity.
Figure 21:
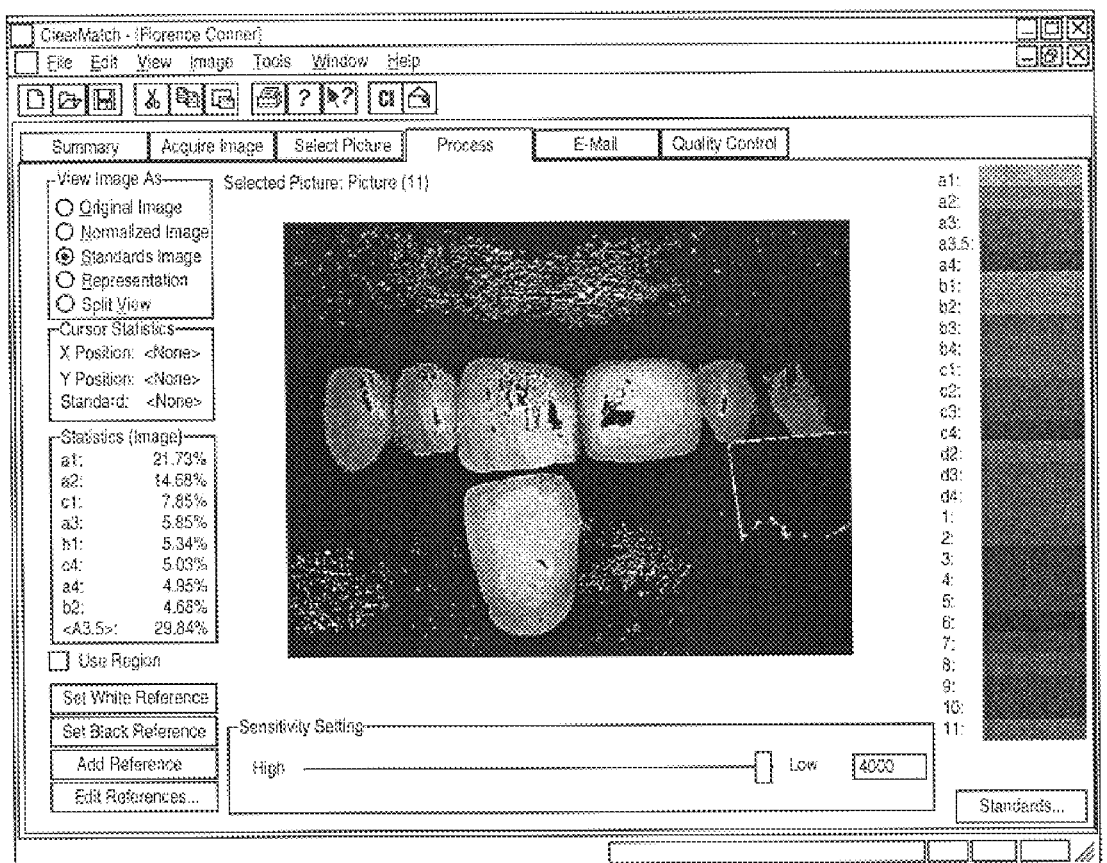
FIG. 21 is a screen capture illustrating a standardized image 46 of FIG. 7 with low sensitivity.

It should be noted that the standardized image 160 is displayed alongside a statistical analysis 162 of the percentage of the standardized image 160 occupied by the various dental shade standards. This statistical analysis 162 may also be confined to a selected region by checking a "Use Region" check box 110. FIGS. 20 and 21 illustrate screen captures of standardized images with medium and low sensitivities, respectively.

Figure 22:
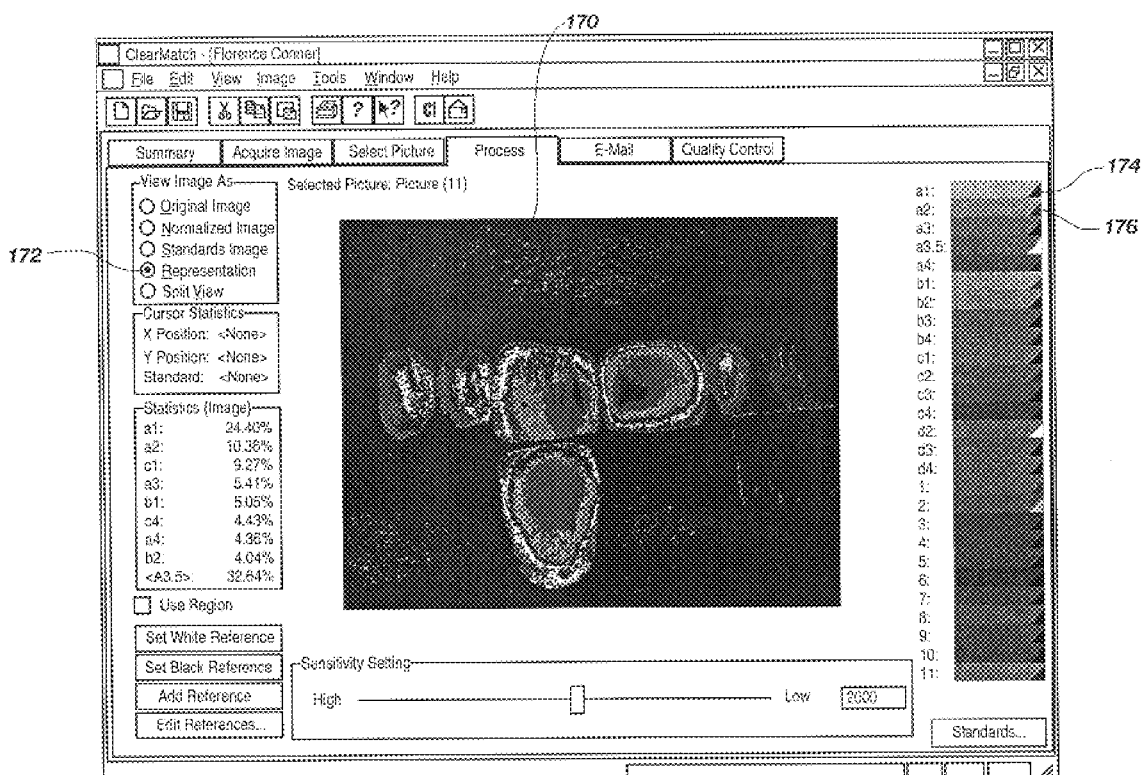
FIG. 22 is a screen capture illustrating the map pseudo-colors to standardized image step 48 of FIG. 7.
Figure 27:
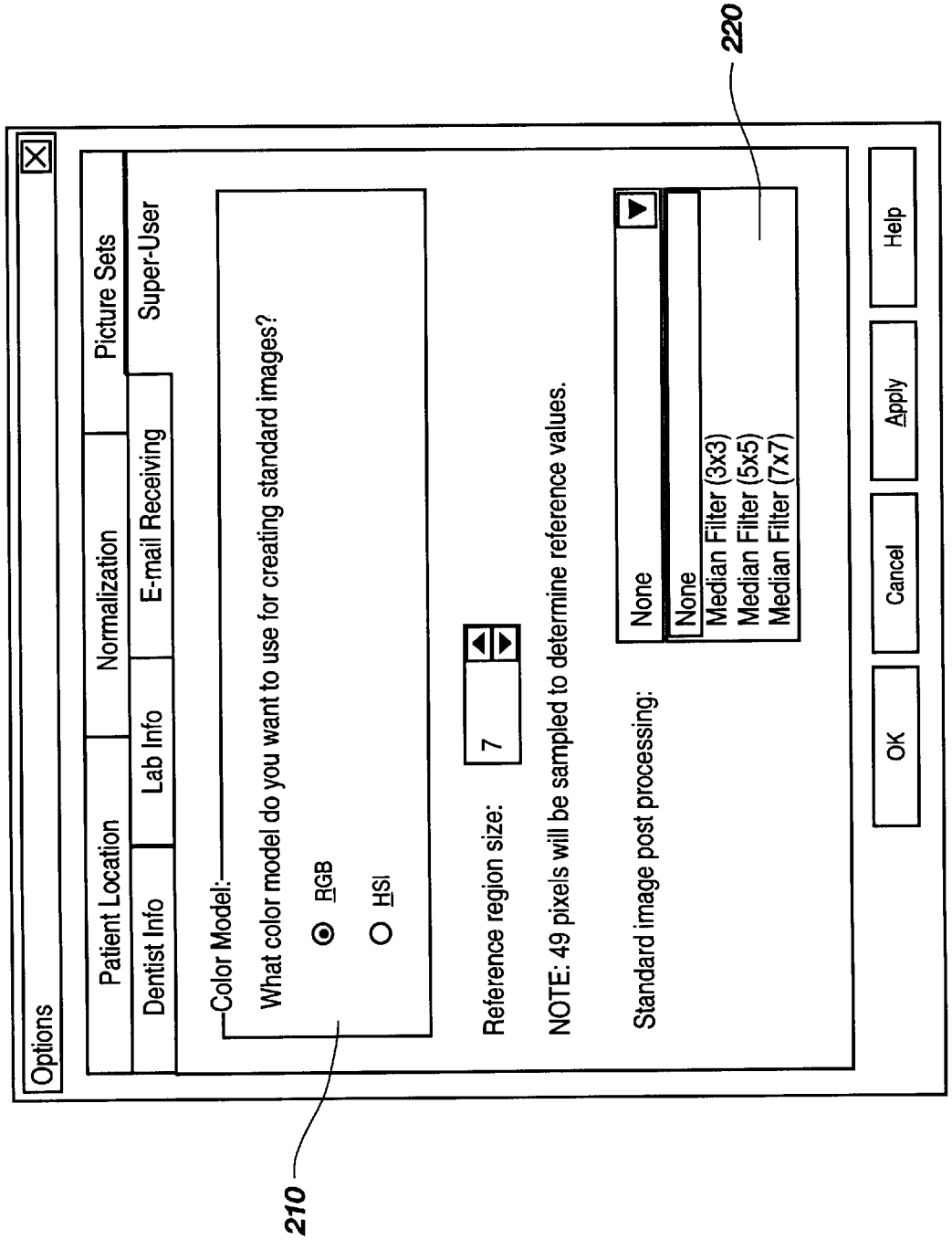
FIG. 27 is a screen capture illustrating a means of selecting between RGB and HSI color models and means for selecting image processing filters according to the preferred embodiment of the invention.

As shown in FIG. 7, once a standardized image is obtained, pseudo-colors may be mapped to the standardized image. Referring to FIG. 22, pseudo-colors may be assigned to each dental shade standard to generate a pseudo-color image (or map) 170 in which the differences between various standards are easier to discern than in the standardized image 160 of FIG. 19. According to the preferred embodiment, the user may obtain a pseudo- color image 170 by selecting a "Representation" view 172, as shown in FIG. 22. Thus, for example, a standard shade "a1", which may be a light tan color, may be assigned a pseudo-color of red 174, while a standard shade "a2", which may be a slightly darker tan color, may be assigned a pseudo-color of grass green 176. The pseudo-colors assigned to each dental shade standard are shown in triangles in the lower right hand corner of each original dental shade standard as illustrated in FIG. 22. As a result of assigning pseudo-colors to each dental shade standard, while the distinctions between "a1" (light tan color) and "a2" (slightly darker tan color) may be difficult to discern from the standardized image 70, they readily stand out in the pseudo-color image 170 because of the contrasting red and grass green colors. Standard image processing filters may also be used with the pseudo-color images to blur or smooth the boundaries between colors to allow a lab technician to "paint" the desired colors on the dental prosthetic. FIG. 27 illustrates a screen capture illustrating a preferred embodiment of a means 220 for selecting various image processing filters to smooth the pseudo-color images. Any other means suitable for providing the user with a selection of image processing filters or means to adjust the parameters of image processing filters for smoothing images may be used with the invention.

Figure 23:
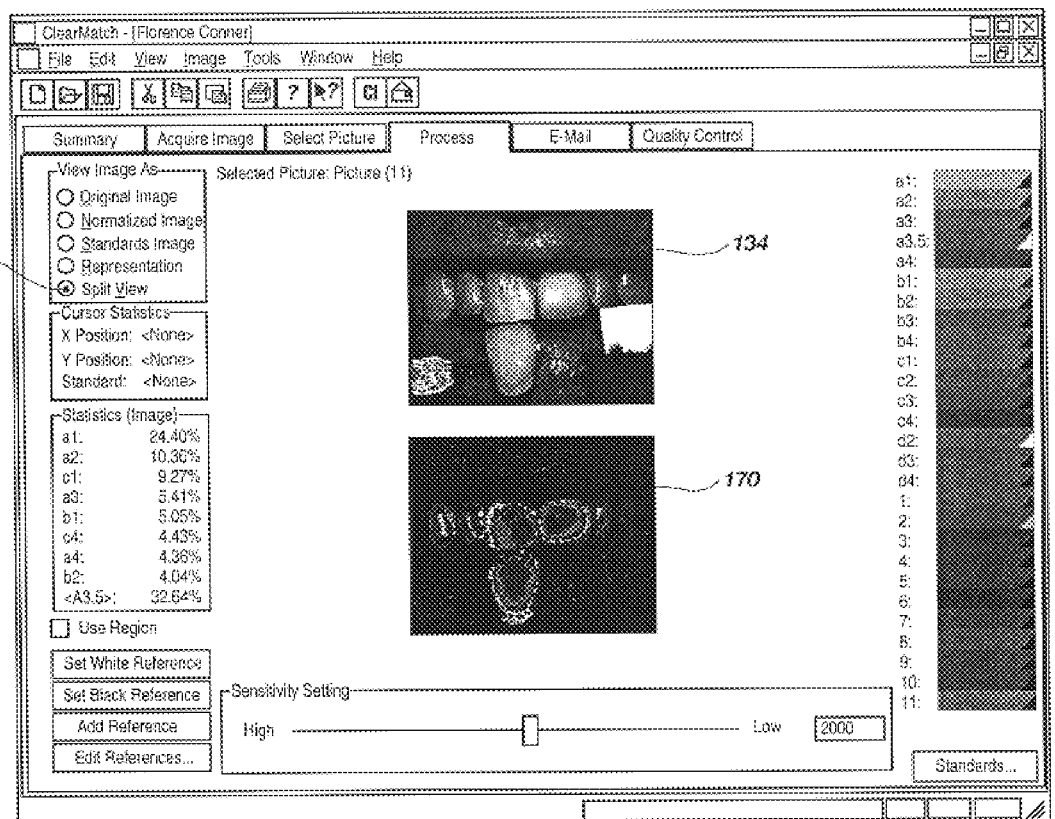
FIG. 23 is a screen capture illustrating a split view of the normalized image of FIG. 14 along side the pseudo-color image of FIG. 20.

An additional feature of the electronic system 56 is the capability of viewing both the normalized image 134 and the pseudo-color image 170 simultaneously. Referring to FIG. 23, a screen capture of a "Split View" is shown with the normalized image 134 shown above the pseudo-color image 170. In the preferred embodiment, the user may view both images (134 and 170) shown in FIG. 23 by selecting "Split View" radio button 180.

As shown in FIG. 2, once the patient images have been analyzed 24, the lab technician manufactures the dental prosthetic 26 using either the standardized image 160 (FIG. 19) or the preferred pseudo-color image 170 (FIG. 22) as a guide.

Once the dental prosthetic is manufactured 26, the lab technician and/or dentist may optionally confirm the color match quality of the dental prosthetic before the dentist installs the prosthetic. Referring to FIG. 24, the software in the electronic system 56 allows either the lab technician or dentist to confirm the color match quality of the prosthetic tooth 190 relative to a surrounding natural tooth 192 by comparing a normalized image of the prosthetic tooth 194 with a normalized image of the patient's natural tooth 196 using the software. The preferred embodiment, it is assumed that the lab technician performs the quality control step 27.

In the preferred embodiment, the lab technician selects a "Quality Control" tab 188 to display a gallery of digital images including a normalized image of the prosthetic tooth 194 after it has been manufactured. Specifically, the lab technician selects the normalized image of the prosthetic tooth 194 and it is displayed below the normalized image of the patient's natural tooth 196. The lab technician then selects the natural tooth 192 and the prosthetic tooth 190 using selection regions 198 and 200, respectively. The electronic system 56 then calculates the average difference 202 (shown in a dashed box) in shades between the two regions 198 and 200 and displays the difference on the display. A dentist may specify that the prosthetic tooth must not exceed a certain maximum average difference (e.g., 10%), and the dental laboratory may charge different fees for prosthetic teeth guaranteed to fall below certain maximum average differences (e.g, $500 for 2%, $300 for 5%, $150 for 10%, etc.)

Once the lab technician has confirmed that the prosthetic tooth meets the specified quality standard, the technician can send an image of the prosthetic tooth to the dentist so the dentist can confirm the quality of the tooth using his own software in the same manner as described immediately above. The dentist can then contact the patient so that the dentist and patient can confer and agree as to the acceptability of the prosthesis. The dentist may confer in-person with the patient or may transmit the image to the patient by electronic mail for review and discussion. If changes are required, those can be conveyed to the lab technician for implementation into the image for final review before the actual prosthetic tooth is completed. Once the dentist authorizes delivery of the prosthetic tooth, the lab technician sends the tooth to the dentist, and the dentist installs the tooth in the patient.

An additional feature of the invention is the capability to e-mail digital images, text or data using the electronic system 56 of the invention. For example, a dentist may take one or more pictures of the patient's mouth and the teeth surrounding the tooth to be replaced. The dentist may then use the electronic system 56 to e-mail the one or more images to a potentially remote dental laboratory for the lab technician to perform the tooth shade analysis 24, manufacture the tooth 26, perform the quality control function 27 and then send the quality control results to the dentist via email. Alternatively, the lab technician may perform the above steps up until the quality control step, and then send a digital image of the manufactured dental prosthetic to the dentist who may then perform the quality control function 27 and if satisfied, install the dental prosthetic 28.

Figure 25:
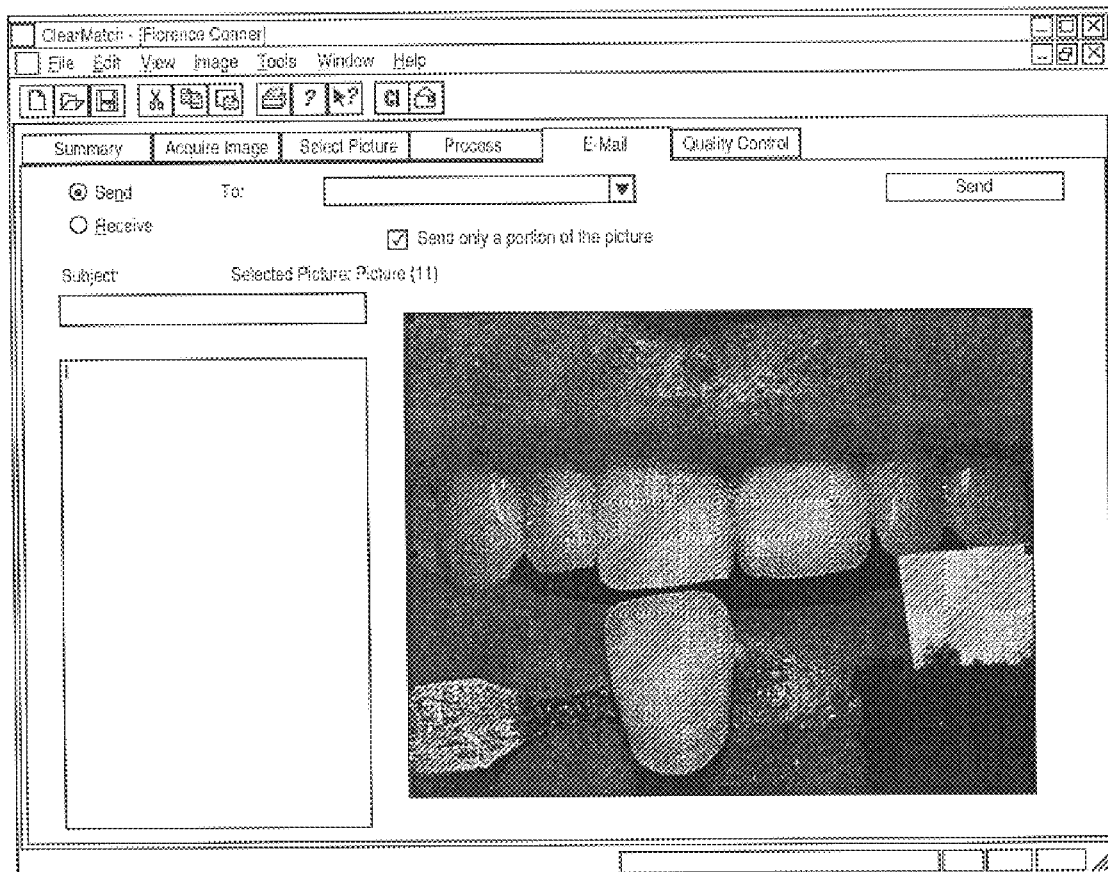
FIG. 25 is a screen capture illustrating electronic mail means of communicating image analysis information and/or an analyzed patient image to a laboratory for manufacturing of a dental prosthetic in accordance with the invention.

Referring to FIG. 25, a screen capture is shown illustrating an electronic mail means of communicating image analysis information and/or a patient image between a dentist office and a laboratory and vice versa for manufacturing of a dental prosthetic in accordance with the invention. Various embodiments of an e-mail feature are contemplated. One embodiment includes the capability to send and receive images along with text messages. This embodiment is particularly suited to the context where the dentist merely takes the patient's photographs and sends the images along with a note or instructions to the lab technician who performs the analysis. Another embodiment would further include the capability to send and receive analysis information such as that which is calculated and displayed during the color analysis. This embodiment may be useful in the context of the dentist performing the tooth shade analysis and sending the processed images, color maps, or other information to the lab technician who would then manufacture the tooth. Another embodiment may include a color composition analysis for manufacturing a dental prosthetic based on color composition. The e-mail feature may, in any case, be used to communicate with the other party, e.g., querying for status, i.e., when a tooth will be delivered, or to ask questions about the details of what the patient wants, etc.

It should be understood that while this invention has been described with respect to a process for manufacturing a prosthetic tooth or bridge or dentures, the system is equally applicable to restoration of teeth in the dentist's office when, for example, a patient's tooth is broken, chipped or otherwise modified from its original condition. In such instances, the dentist may prepare the image and analyze it within his office to determine an accurate restoration of the tooth. The system of the invention is equally applicable to a process for teeth whitening. In such a process, the image analysis procedures described herein are used to determine the shade of a patient's teeth, and then to compare the shade of the post-whitening teeth to the shade of the pre-whitening teeth.

It should also be understood that while this invention has been described with respect to colors described in the RGB color model, the invention may alternatively incorporate any other applicable color models for describing colors. Other color models which may be suitable for use with this invention include: Hue, Saturation, Intensity (HSI) and its variants, (e.g., Hue Saturation Value (HSV), Hue Saturation Luminance (HSL), Hue Value Chroma (HVC) and Hue Saturation Darkness (HSD)), television transmission color models (e.g., YIQ, YUV, YCbCr and YCC), and CIE color models (e.g., CIELUV and CIELAB). The HSI color model is presently the preferred color space for this invention because separation of the intensity component of the color format is advantageous for image processing.

The software of the invention may allow the user to select between RGB and HSI or other color models for representing colors in the processing described herein. Referring again to FIG. 27, a screen capture illustrating a preferred embodiment of a window for selecting the color model is shown. The currently preferred embodiment of a system of the invention allows the user to select 210 between RGB and HSI color models.

The HSI color model is a linear transformation of the RGB color model. The following equations are useful for converting RGB data to HSI data:

$$H = \frac{1}{2\pi}\left(\frac{\pi}{2} - \arctan\left\{\frac{(2R - G - B)}{\sqrt{3}(G - B)}\right\} + \pi\right) \text{ for } G < B \quad (8)$$

$$S = 1 - \left[3\frac{\min(R, G, B)}{R + G + B}\right] \quad (9)$$

$$I = \frac{R + G + B}{3} \quad (10)$$

where min(R,G,B) is the minimum of the three R, G, B values. A preferred embodiment of the electronic system includes the capability to switch between RGB and HSI color models.

Although this invention has been described with reference to particular embodiments, the invention is not limited to these described embodiments. For example, while the various steps and procedures of the methods of this invention have been described as occurring in a particular order, the invention is not limited to the described order. Rather, the invention is limited only by the appended claims, which include within their scope all equivalent devices or methods that operate according to the principles of the invention as described.

What is claimed is:

1. A method of effecting a dental repair or replacement, the method comprising:
    acquiring at least one image of a patient's tooth, said at least one image containing normalization references;
    normalizing said at least one image in accordance with said normalization references;
    standardizing said at least one normalized image by matching said at least one normalized image to selected shade standards, according to a selected color model; and
    producing a restorative modification of said patient's tooth in accordance with said standardized image.

2. The method of claim 1, further including acquiring said at least one image containing black and white normalization references.

3. The method of claim 2, further including acquiring said at least one image containing at least one color reference.

4. The method of claim 1, wherein acquiring said at least one image includes acquiring the at least one image using an input device selected from the group consisting of a digital camera, an analog camera, a scanner, an Internet connection, a modem and a computer-readable storage medium.

5. The method of claim 1, wherein said selected color model is a Red-Green-Blue (RGB) color model.

6. The method of claim 1, wherein said selected color model is a Hue Saturation Intensity (HSI) color model.

7. The method of claim 1, further comprising converting from one color model to another color model.

8. The method of claim 1, wherein said producing said restorative modification of the patient's teeth comprises manufacturing a dental prosthetic.

9. The method of claim 8, wherein acquiring said at least one image, normalizing said at least one image, standardizing said at least one normalized image, and making said dental prosthetic occur in sequential order.

10. The method of claim 8, further comprising comparing average Red, Green, and Blue values of an image of said dental prosthetic with average Red, Green, and Blue values of said standardized image.

11. The method of claim 1, further comprising sending said at least one acquired image to a dental laboratory using a delivery means selected from the group consisting of electronic mail, an Internet connection, a modem-to-modem connection, and a computer-readable storage medium.

12. The method of claim 1, wherein said normalizing said at least one image in accordance with said normalization references includes normalizing a look-up table associated with said at least one image.

13. The method of claim 1, wherein standardizing said at least one normalized image comprises:
    selecting a standardization sensitivity level;
    determining a color distance between Red, Green, and Blue values associated with each pixel of said at least one normalized image and each color of said selected shade standards;
    determining a minimum color distance for each pixel; and
    for each pixel, when the minimum color distance for the pixel is less than said selected standardization sensitivity level, matching the particular selected shade standard associated with the minimum color distance to the pixel.

14. The method of claim 1, wherein said selected shade standards includes incisal tooth shade standards.

15. The method of claim 1, further comprising mapping pseudo-colors representative of each of said selected shade standards onto said standardized image to form a pseudo-color image.

16. The method of claim 15, further comprising processing said pseudo-color image with an image processing filter to smooth transitions between colors.

17. The method of claim 1, wherein said producing said restorative modification of said patient's tooth comprises repairing a broken, chipped or damaged tooth.

18. The method of claim 1, further comprising communicating digital images between a dentist office and a dental laboratory where said prosthetic is manufactured.

19. The method of claim 18, wherein said communicating is performed by electronic mail.

20. The method of claim 1, further comprising installing said restorative modification in said patient's mouth.

21. A method of whitening a patient's teeth, comprising:
    acquiring at least one pre-whitening image of the patient's teeth containing first normalization references;
    normalizing said at least one pre-whitening image in accordance with said first normalization references;
    standardizing said at least one normalized, pre-whitening image by matching said at least one normalized, pre-whitening image to selected shade standards;
    whitening the patient's teeth;
    acquiring at least one post-whitening image of the patient's teeth containing second normalization references;

normalizing said at least one post-whitening image in accordance with said second normalization references;

standardizing said at least one normalized post-whitening image by matching said at least one normalized post-whitening image to selected shade standards; and comparing said at least one standardized pre-whitening image and said at least one standardized post-whitening image.

22. The method of claim 21, wherein said first normalization references and said second normalization references each include:

a black reference, a white reference, and at least one color reference.

23. A method of performing image analysis on a patient's teeth, comprising:

acquiring at least one image of the patient's teeth containing normalization references including
a black reference,
a white reference, and
at least one color reference;

normalizing said at least one image in accordance with said normalization references; and standardizing said at least one normalized image by matching said at least one normalized image to selected shade standards.

24. A computer-readable storage medium containing computer program instructions for causing a computer to operate in accordance with a method for performing image analysis on a patient's teeth, said computer program instructions configured for causing said computer to:

acquire at least one image of the patient's teeth said at least one image containing normalization references, said normalization references including
a black reference,
a white reference, and
at least one color reference;

normalize said at least one image in accordance with said normalization references; and standardize said at least one normalized image by matching said at least one normalized image to selected shade standards.

25. An apparatus for performing image analysis on a patient's teeth, comprising:

an input device for acquiring at least one image of the patient's teeth containing normalization references; and a processor device coupled to the input device, said processor device configured for normalizing said at least one image in accordance with the normalization references contained therein and matching the normalized image to selected shade standards to standardize said at least one normalized image.

26. The apparatus of claim 25, wherein said normalization references include:

a black reference;

a white reference; and at least one color reference.

27. The apparatus of claim 25, wherein the input device is selected from a group comprising a digital camera, an analog camera, a scanner, an Internet connection, a modem and a computer-readable storage medium.

28. The apparatus of claim 25, wherein said processor device comprises a digital signal processor.

29. The apparatus of claim 25, further comprising an output device for displaying information related to the image analysis.

30. The apparatus of claim 25, further comprising a memory device in communication with said processor device for storing a computer program implementing a method of effecting a dental repair or replacement, said method comprising:

acquiring an image of a patient's tooth using said input device said image containing said normalization references;

normalizing said image in accordance with said normalization references;

standardizing said normalized image by matching said normalized image to selected shade standards, wherein said shade standards include incisal tooth shade standards; and producing a restorative modification of said patient's tooth in accordance with said standardized image.

31. An electronic system for performing image analysis of a patient's teeth, the electronic system comprising:

an input device for acquiring an image of said patient's teeth said image containing normalization references;

a processor device coupled to said input device for performing image analysis on said image in accordance with a method of tooth shade matching;

a memory device coupled to said processor device for storing a computer program implementing said method of tooth shade matching;

an output device coupled to said processor device for displaying results of the image analysis responsive to said method of tooth shade matching; and a storage device coupled to said processor device for storing data.

32. The electronic system of claim 31, wherein the processor device comprises a computer system.

33. The electronic system of claim 31, wherein the processor device comprises a digital signal processor.

34. The electronic system of claim 31, wherein said normalization references include:

a black reference;

a white reference; and at least one color reference.

35. The electronic system of claim 31, wherein said method of tooth shade matching includes:

acquiring an image of a patient's tooth from said input device said image containing said normalization references;

normalizing said image in accordance with said normalization references;

standardizing said normalized image by matching said normalized image to selected shade standards, wherein said shade standards include incisal tooth shade standards; and producing a restorative modification of said patient's tooth in accordance with said standardized image.

* * * * *

UNITED STATES PATENT AND TRADEMARK OFFICE
CERTIFICATE OF CORRECTION

PATENT NO. : 6,328,567 B1  Page 1 of 1
DATED : December 11, 2001
INVENTOR(S) : Alan C. Morris and Craig A. Mabrito It is certified that error appears in the above-identified patent and that said Letters Patent is hereby corrected as shown below:

Column 3,
Line 5, change "Lehmann" to -- Lehmann, --

Column 4,
Line 62, after "picture" delete "38"

Figure 1:
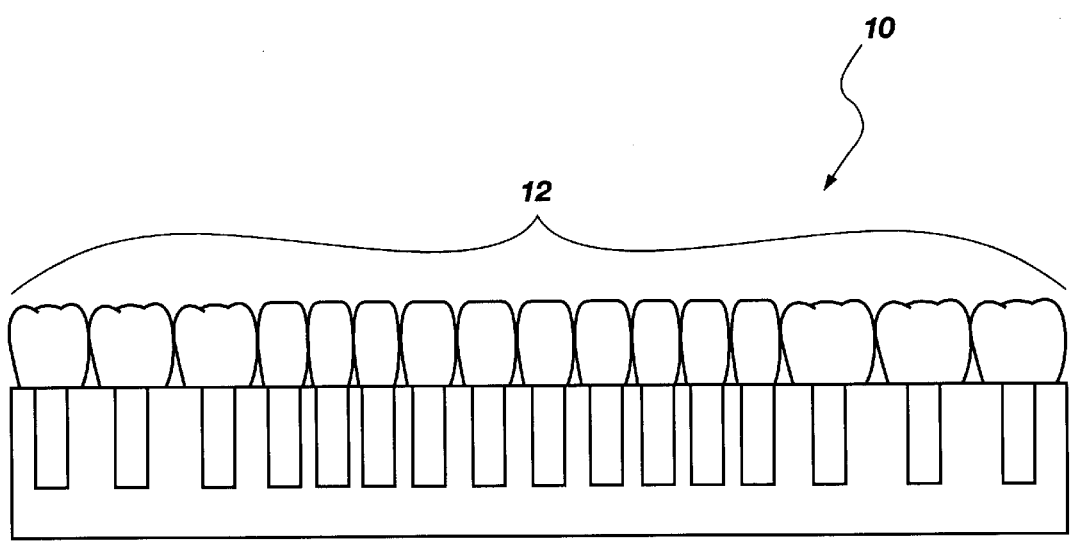
FIG. 1 is a side view of a conventional shade guide.

Column 5,
Line 10, change "FIG. 1" to -- FIG. 11 --

Column 11,
Line 5, change "embodiment" to -- embodiment, --
Line 23, change "example" to -- example, --
Line 59, change "convenience' to -- convenience, --

Column 13,
Line 5, change "70" to -- 160 --

Column 14,
Line 22, change "and" to -- and, --

Signed and Sealed this

Twenty-third Day of September, 2003

JAMES E. ROGAN
*Director of the United States Patent and Trademark Office*